United States Patent
Coffindaffer et al.

(10) Patent No.: US 11,052,556 B2
(45) Date of Patent: Jul. 6, 2021

(54) SHAVE CARE COMPOSITION FOR A LIQUID DISPENSING RAZOR

(71) Applicant: The Gillette Company, Boston, MA (US)

(72) Inventors: Timothy Coffindaffer, Maineville, OH (US); Benjamin P Heath, Loveland, OH (US); Kenneth E Kyte, Oregonia, OH (US); Katharine A Bakes, Cincinnati, OH (US); Joseph A DePuydt, Loveland, OH (US)

(73) Assignee: The Gillette Company LLC, Boston, MA (US)

( * ) Notice: Subject to any disclaimer, the term of this patent is extended or adjusted under 35 U.S.C. 154(b) by 349 days.

(21) Appl. No.: 14/529,359

(22) Filed: Oct. 31, 2014

(65) Prior Publication Data

US 2015/0121705 A1    May 7, 2015

Related U.S. Application Data

(60) Provisional application No. 61/898,870, filed on Nov. 1, 2013.

(51) Int. Cl.
| | |
|---|---|
| B26B 21/44 | (2006.01) |
| A61K 8/891 | (2006.01) |
| A61K 8/06 | (2006.01) |
| A61K 8/368 | (2006.01) |
| A61K 8/37 | (2006.01) |
| A61K 8/81 | (2006.01) |
| A61K 8/92 | (2006.01) |
| A61Q 9/02 | (2006.01) |

(52) U.S. Cl.
CPC .............. *B26B 21/446* (2013.01); *A61K 8/06* (2013.01); *A61K 8/368* (2013.01); *A61K 8/37* (2013.01); *A61K 8/8158* (2013.01); *A61K 8/891* (2013.01); *A61K 8/92* (2013.01); *A61Q 9/02* (2013.01); *A61K 2800/48* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 5,283,952 A * | 2/1994 | Mock | B26B 21/446 30/41 |
| 8,209,867 B2 * | 7/2012 | Clarke | B26B 21/4018 30/34.2 |
| 8,563,491 B2 | 10/2013 | Coffindaffer et al. | |
| 2002/0023351 A1 | 2/2002 | Simms | |
| 2006/0254056 A1 | 11/2006 | Coffindaffer et al. | |
| 2007/0137042 A1 * | 6/2007 | Focht | A61K 8/31 30/34.05 |
| 2009/0126197 A1 * | 5/2009 | Tomassetti | B26B 21/446 30/41 |
| 2010/0272667 A1 | 10/2010 | Kyte, III et al. | |
| 2011/0262370 A1 | 10/2011 | Kyte, III et al. | |
| 2011/0272320 A1 * | 11/2011 | Alwattari | A61K 8/046 206/524.1 |
| 2012/0102744 A1 | 5/2012 | Forsdike et al. | |
| 2012/0103151 A1 | 5/2012 | Jones et al. | |
| 2013/0045256 A1 | 2/2013 | Schwartz | |
| 2013/0097868 A1 | 4/2013 | Jessemey et al. | |

FOREIGN PATENT DOCUMENTS

JP    2001/316233    11/2001

OTHER PUBLICATIONS

PCT International Search Report and Written Opinion for PCT/US2014/063452 dated Feb. 13, 2015.

* cited by examiner

*Primary Examiner* — Patricia Duffy
*Assistant Examiner* — Garen Gotfredson
(74) *Attorney, Agent, or Firm* — Kevin C. Johnson

(57) ABSTRACT

A liquid dispensing razor including a reservoir containing a shave care composition. The shave care composition comprises water; one or more lipophilic skin conditioning agents; one or more thickening agents including electrolyte sensitive polymers; one or more emulsifying agents; and one or more lubricants. The shave care composition is delivered to the skin by the razor to provide skin comfort and moisturization benefits during the shave. The combination of the chemistry in the razor results in step change in skin condition in consumer and technical skin moisturization benefits.

18 Claims, 11 Drawing Sheets

SHAVE CARE COMPOSITION FOR A LIQUID DISPENSING RAZOR

BACKGROUND OF THE INVENTION

Several different composition dispensing razors are known. See, e.g., U.S. Pat. Nos. 7,007,389; 6,308,413; 4,753,006; 4,635,361; 6,986,207; 5,855,066; and 4,129,942. These and other dispensing razors have been described as being capable of dispensing various types of shaving related preparations, including clear or translucent shaving gels or lotions.

For example, composition dispensing shavers having a plurality of shaver heads with rotary blade cutters capable of dispensing a lubricant for allegedly decreasing friction between the shaving heads and cutters with skin has been disclosed in U.S. Patent Publ. No. 2008/0216322 and RE038934. Additionally, Phillips Norelco recently marketed a composition dispensing razor under the name of Cool Skin Shaver®. This shaver has a large main head containing multiple rotary blades and dispenses a Nivea For Men® moisturizing shave lotion out of the center of the rotary blades, allowing the composition to coat the shaving head and cutters to allegedly decrease friction with skin. Kits comprising razors and moisturizing compositions have also been disclosed. See e.g. US Publication No. 2007/0137042 and 2008/0317697.

A runny or less viscous formulation may be desirable in certain instances, such as where the formulator wants the composition to dispense in a discrete area but quickly spread to contact and/or coat a large surface, such as the shaving head and cutters. It can also be desirable, however, for the product to be sufficiently thick to suspend dispersed phase materials (e.g., emulsions, particles) or so it will not run off or otherwise be pushed away from the portion of skin desired for treatment. Many different types of thickeners and viscosity modifying agents can impact the viscosity and rheology of the composition. Many of these ingredients, however, also impact other characteristics of the composition when added, such as making the composition stringy or tacky, or making the composition cloudy or opaque. Examples of numerous clear and/or non-foaming skin care compositions of varying thickness and viscosity are known. See e.g. WO 93/18740; GB 2236760; U.S. Pat. Nos. 2,833,693; 3,072,536; 4,585,650; 4,917,844; and 6,627,185.

The number of combinations of devices and compositions is numerous. In addition, if one were to further consider the many different types of personal care compositions which can be used, the number of executions can be near limitless. Despite the near limitless number of potential combinations of features, there remains a need for a composition dispensing device capable of dispensing a composition that can help reduce skin irritation and dry skin and improve shave closeness.

Improved shave preparations that address these problems are desired in the art. This invention addresses these needs by coupling chemistry in the razor providing lubrication at the point at which it is needed and conditioning the skin during the shave when the skin is at its most vulnerable state to deliver post shave skin and conditioning benefits.

SUMMARY OF THE INVENTION

A liquid dispensing razor including a reservoir containing a shave care composition. The shave care composition comprises water; one or more lipophilic skin conditioning agents; one or more thickening agents including electrolyte sensitive polymers; one or more emulsifying agents; and one or more lubricants. The shave care composition is delivered to the skin by the razor to provide skin comfort and moisturization benefits during the shave. The advantage of including electrolyte sensitive polymers in the shave care composition chemistry is its ability to "drop out" the benefit ingredients during shaving to improve functionality or efficacy. The electrolyte sensitive polymer loses suspension capability in the presence of very little electrolyte (salt in water, surfactant left on the skin, electrolyte on the skin) causing the formula to release key lubricating and conditioning ingredients. The emulsifying agents work in concert with this "drop-out" behavior to even out spreading across the cartridge/skin and also to enhance deposition of the dispersed phase ingredients onto the skin. The combination of the chemistry in the razor results in step change in skin condition in consumer and technical skin moisturization benefits.

Other features and advantages of the invention will be apparent from the description and drawings, and from the claims.

DETAILED DESCRIPTION OF THE INVENTION

Figure 1:
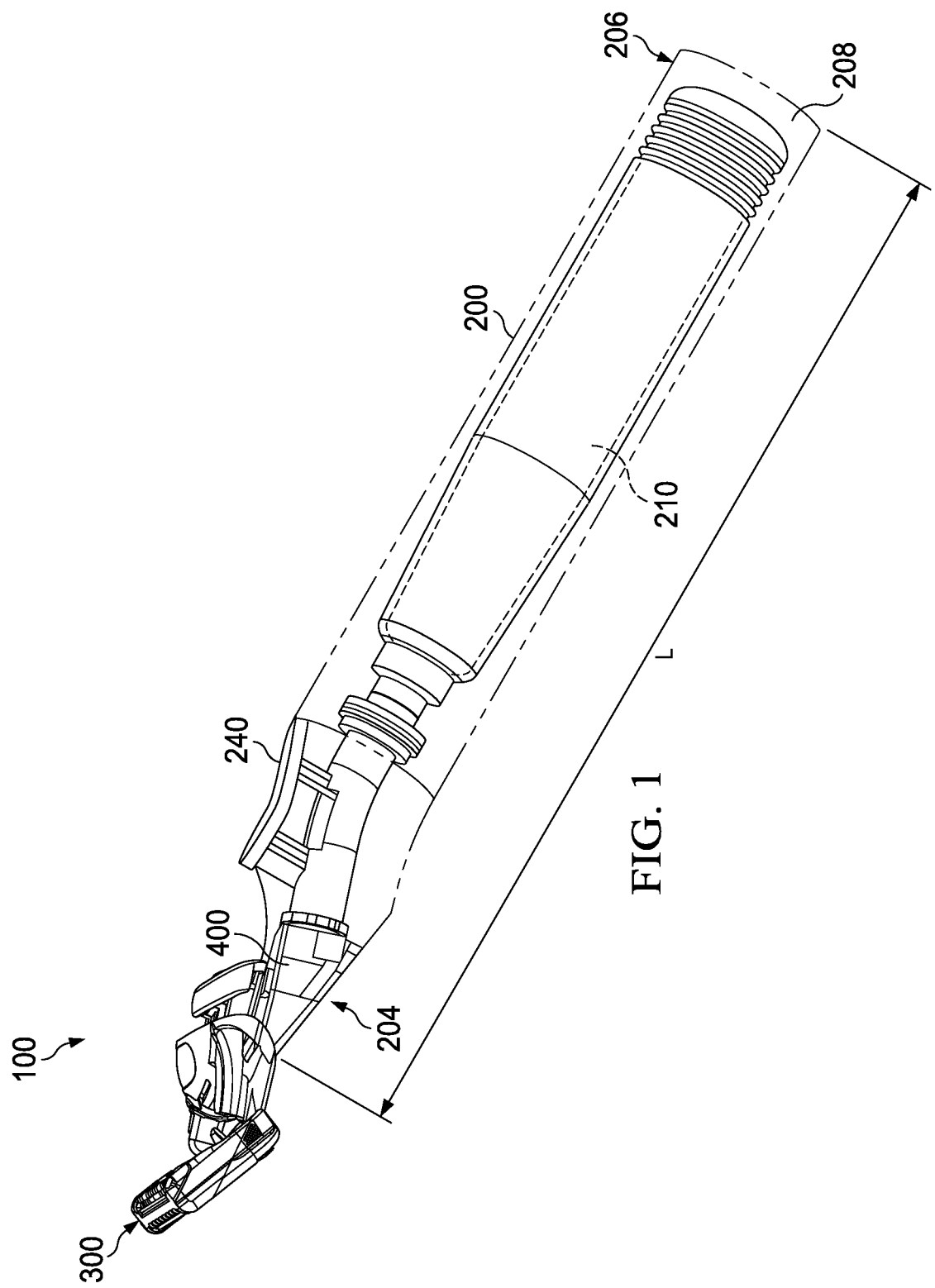
FIG. 1 is a side view of a wet shaving razor of the present invention.

It has been found that when selecting a composition to be used in a liquid dispensing razor, it can be particularly desirable to select a composition which is sufficiently thick and viscous that it will not run off the skin or razor after being dispensed. This is balanced by the need for the composition to be sufficiently thin in order to be capable of being dispensed via a pump which requires continuous flow from a reservoir to the razor during actuation of the pump and ensure that the entire contents of the reservoir is evacuated during use. Additionally, moisturizing compositions can be desirable for use in a composition dispensing razor to allow for multiple benefits, including but not limited to hydration of the hairs prior to shaving, moisturization of skin during the hair removal process, lubrication of skin to reduce friction during the shave, and so forth. Those of skill in the art will understand that moisturization can include hydration of the skin or hair or lubrication of the hair or skin to increase glide and reduce friction between the composition dispensing device and skin.

1. Shave Care Composition:

The current invention provides for shave care composition for a liquid dispensing razor (LDR) having desirable properties that improve the shave experience. Without wishing to be bound by theory, it is believed that the compositions within the shave care preparations of the present invention interact synergistically to provide for an enhanced experience.

The shave care composition of the present invention is rooted in a skin care thickening chemistry coupled with mild nonionic surfactant emulsifiers and lubricating polymers to make it more suitable for shaving application. Specifically, the surfactant improves spreading, wetting and rinseablity while the lubricants aid in protection and glide during the shaving process. Furthermore, the shave care composition contains glycerin and a dispersed phase lipid composed of hydrophobic oils which smoothes, conditions and locks-in moisture. More generally, the composition is a chemistry platform upon which a large number of chemistry variants (and derived benefits to the consumer) can be delivered.

The advantage of the shave care composition chemistry revolves around the formula being able to suspend key benefit agents (e.g. dispersed phase conditioning oils) within a continuous, water plus polymer dominated continuous phase. The system's rheological behavior is governed primarily by this continuous phase. This property allows a wide range (both type and level) of benefit ingredients to be suspended in the dispersed phase and still maintain a consistent fluid property/behavior in the liquid dispensing razor plumbing fully described below.

Another advantage of the shave care composition chemistry is its ability to "drop out" the benefit ingredients from the dispersed phase only during shaving to improve functionality or efficacy. This is accomplished by using an electrolyte sensitive polymer that loses suspension capability in the presence of very little electrolyte (e.g. salts in water, surfactant left on the skin, electrolyte on the skin). The formula then releases the key lubricating and conditioning ingredients. The low levels of emulsifying surfactant work in concert with this "drop-out" behavior to even out spreading across the cartridge/skin and also enhance deposition of the dispersed phase ingredients onto the skin.

Water

The shave care composition of the current invention comprises water. In one embodiment, the shave care composition comprises at least about 30% by weight water. In an alternate embodiment, the shave care composition comprises at least about 40% by weight water. In an alternate embodiment, the shave care composition comprises at least about 50% by weight water.

Lipophilic Skin Conditioning Agent

Shave care composition of the present invention employ one or more lipophilic skin conditioning agents. The concentration level of the skin conditioning agents either singularly or collectively may range from about 1% to about 50% by weight of the base composition. Some preferred concentration levels include greater than about 5%, from about 10% to about 40%, and from about 13% to about 30%. It is to be understood that the scope of appended claims that do not specify a concentration level of the lipophilic skin conditioning agent is not limited to the levels described in this paragraph.

Exemplary skin conditioning agents include hydrocarbons, polymeric hydrocarbons, esters, ethers, and silicones selected from the group consisting of alkyl ethers, mineral oil, isoparaffin, greater than C20 hydrogenated polyisobutene; and an ester composed of a branched C16-C22 alkyl chain and a mono alkyl group consisting of a linear or branched C1 to C6 alkyl chain. Some preferred skin conditioning agents comprise isostearic acid derivatives; for example, isostearyl isostearate, isopropyl isostearate, isopropylpalmitate, isopropylmyristate, PPG-15 Stearyl Ether, petrolatum, dimethicone and dimethiconol and mixtures thereof. Other skin conditioning agents known to the skilled artisan may also be employed depending on the form of the personal care composition and the targeted skin benefit.

In one embodiment, two or more hydrocarbon phases are preblended prior to emulsification. It has been found that pre-blends of such ingredients can lead to improved skin feel. Examples include petrolatum blended with mineral oil or isopropylpalmitate.

The skin conditioning agents may also help to reduce the coefficient of friction for personal care compositions provided herein that are in the form of shaving compositions. The reduction in friction can decrease the potential for skin irritation that can arise from contacting the skin one or more times with a razor blade. Employment of the skin conditioning agent in this context may also permit formulation flexibility regarding the type and concentration level of lubricants (as discussed more fully below) that are included in the shaving preparations.

In one embodiment of the invention, particle size of the dispersed phase skin conditioners has a average particle size of 95% of the dispersed phase mass below 20 microns, preferably below 15 microns, more preferably below 10 microns and most preferably below 5 microns. Particle size as measured using a Horiba particle size analyzer and reported as D 50 values. While not wishing to be bound by theory, the smaller particle size is very important for the dispersed phase skin conditioners to be retained on the skin during shaving especially when the shaving composition is dispensed in front of the razor blades or upon re-stroke of the razor when the composition has been deposited on the skin. It is recognized that the skin is not a flat surface and smaller particles can deposit and reside in the recessed areas of the skin and around the hair follicle more easily than larger particles.

Thickening Agent

The shave care composition of the present invention contain one or more thickening agents, from about 0.1% to about 5%, alternatively from about 0.1% to about 4%, alternatively from about 0.25% to about 3%, by weight of the composition.

Nonlimiting classes of thickening agents include those selected from the following: Carboxylic Acid Polymers, Crosslinked Polyacrylate Polymers Polyacrylamide Polymers, Polysaccharides, Clays and Gums, and mixtures thereof when appropriate.

In one embodiment, compositions of the present invention include a thickening agent selected from carboxylic acid polymers, crosslinked polyacrylate polymers, polyacrylamide polymers, polysaccharides, and mixtures thereof, more preferably selected from carboxylic acid polymers, polyacrylamide polymers, polysaccharides, and mixtures thereof.

Preferred thickening/suspending agents include electrolyte sensitive polymers that are shear thinning when in solution. Shear thinning is property that makes a liquid easy to spread and pump. We have found that electrolyte sensitive polymers have desired performance profiles. While not wishing to be bound by theory, the electrolyte sensitive polymers interact with the residual surfactant or electrolyte left on the skin and release the lubrication agents and/or suspended conditioning agents for spreading across the razor and across the surface of the skin. Preferred electrolyte sensitive polymers include but are not limited to: Polyacrylamide, Hydroxyethyl Acrylate/Sodium Acryloyldimethyltaurate Copolymer, Sodium Acrylate/Sodium Acryloyldimethyl Taurate Copolymer, Ammonium Polyacrylate, Sodium Acrylate/Acryloyldimethyltaurate/Dimethylacrylamide Crosspolymer, Hydroxyethyl Acrylate/Sodium Acryloyldimethyltaurate Copolymer which can be purchased from Seppic or Carboxylic Acid Polymers (Carbomers) such as Ultrez 10, Carbopol 934, Carbopol 980 and ETD 2050 which can be purchased from Lubrizol or Ammonium Acryloyldimethyltaurate/VP Copolymer, Sodium Acryloyldimethyltaurate/VP Copolymer, Ammonium Acryloyldimethyltaurate/Beheneth-25 Methacrylate Crosspolymer, which can be purchased from Clariant. The most preferred electrolyte sensitive polymer is Polyacrylamide available as Sepigel 305 (Polyacrylamide & C13-14 Isoparaffin & Laureth-7).

Emulsifier

The shave care composition of the present invention contain one or more emulsifying agents, from about 0.1% to about 20%, alternatively from about 0.5% to about 15%, alternatively from about 1.0% to about 12%, by weight of the composition.

Nonlimiting examples of surfactants for emulsification for use in the compositions of the present invention are disclosed in McCutcheon's, Detergents and Emulsifiers, North American edition (1986), published by allured Publishing Corporation; and McCutcheon's, Functional Materials, North American Edition (1992). Preferred emulsifiers are nonionic surfactants/emulsifiers. Nonlimiting useful emulsifiers herein include those selected from the group consisting of alkyl glucosides, alkyl polyglucosides, polyhydroxy fatty acid amides, alkoxylated fatty acid esters, sucrose esters, alkoxylated fatty alcohols, amine oxides, and mixtures thereof. Most preferred are alkoxylated fatty alcohols and alkyl glucosides and mixtures thereof.

Lubricants

Shave compositions of the present invention may employ one or more lubricants, from about 0.1% to about 8%, alternatively from about 0.1% to about 5%, alternatively from about 0.2% to about 3%, by weight of the composition.

Exemplary lubricants include lubricous water soluble polymers, water insoluble particles, and hydrogel-forming (or water swellable) polymers, and mixtures thereof.

Useful lubricious water soluble polymers may have a molecular weight greater between about 300,000 and 15,000,000 daltons, preferably more than about one million daltons. Nonlimiting examples of suitable lubricious water soluble polymers include polyethylene oxide, polyvinylpyrrolidone, and polyacrylamide. Nonlimiting useful water insoluble particles may include inorganic particles or organic polymer particles. Hydrogel-forming polymers are typically highly hydrophilic polymers that, in water, form organized three-dimensional domains of approximately nanometer scale. Additional polymer lubricants include: cellulose derivatives such hydroxyalkyl cellulose polymers such as hydroxyethyl cellulose and hydroxypropyl cellulose, carboxymethyl cellulose, and cellulose methyl ether and polysaccharide gums such as, for example, xanthan gum, carrageenan gum, guar gum, locust bean gum, and hydroxypropyl guar gum.

Sensate Ingredients

In one embodiment of the invention, the composition contains sensate molecules, or combinations of sensate molecules. Sensate molecules can be materials that provide the sensation of a thermal change, e.g., heating or cooling. Applicants have found that the addition of sensate molecules using this composition provides longer lasting skin sensation and comfort benefits. Non-limiting examples include: p-Methane-3,8-diol; Isopulegol; Menthoxypropane-1,2,-diol; Curcumin; Menthyl Lactate; Gingerol; Icilin; Menthol; Tea Tree Oil; Methyl Salicylate; Camphor; Peppermint Oil; N-Ethyl-p-menthane-3-carboxamide; N-[4-(Cyanomethyl)phenyl]-2-isopropyl-5-methylcyclohexanecarboxamide; Ethyl 3-(p-menthane-3-carboxamido)acetate; 2-Isopropyl-N,2,3-trimethylbutyramide; Menthone glycerol ketal, and mixtures thereof.

Gel Network

The shave composition is substantially free from a gel network phase. As used herein, the term "gel network" refers to a lamellar or vesicular solid crystalline phase which comprises at least one fatty amphiphile. The present invention contains less than about 3%, alternatively less than about 1%, alternatively less than about 0.5% of at least one fatty amphiphiles. Gel networks have been found to reduce the rinse profile of these systems. Fatty alcohol gel networks have been used for years in cosmetic creams and hair conditioners. Gel networks are a re-solidified liquid crystal gel phase formed by fatty amphiphiles (e.g. cetyl or stearyl alcohol) and a hydrophilic phase (e.g. water). It is formed by undergoing a melting and then re-solidification process in the hydrophilic phase. The gel network will typically have a lower thermal transition than the melt temperature of the fatty amphiphile itself.

Optional Ingredients

The shave care composition can further comprise additional optional ingredients. Suitable additional optional ingredients include perfume, preservatives, chelants, sensates (e.g. menthol), desquamation actives, anti-acne actives, anti-wrinkle/anti-atrophy actives, anti-oxidants/radical scavengers, flavonoids, anti-inflammatory agents, anti-cellulite agents, topical anesthetics, tanning actives, skin lightening agents, skin soothing and healing actives, antimicrobial actives, sunscreen actives, visual skin enhancers, humectants and moisturizing agents (e.g., glycerin, glycols, sorbitol) and the like. Such optional ingredients are described more fully in U.S. application Ser. No. 11/367,918, filed Mar. 3, 2006. Preferred additional optional ingredients include salicylic acid, opacifiers (e.g. mica and titanium dioxide), perfume, hydrophilic conditioning agents (e.g., glycerin) and skin sensates (e.g. menthol).

The shave care composition of the present invention may contain salicylic acid, its isomers, tautomers, salts and derivatives thereof. Alternatively, the compositions comprise from about 0.001% to about 5% salicylic acid. Alternatively, the compositions comprise from about 0.01% to about 2% salicylic acid. Alternatively, the compositions comprise from about 0.1% to about 1% salicylic acid. Without wishing to be bound by theory, it is believed that salicylic acid is efficacious for the treatment of acne on the skin. Moreover, the salicylic acid is capable of treating and/or reducing the presence of acne on the skin. Such treatment with the shave care composition of this invention involves applying the shave care composition to the skin via the razor and shaving the skin that has been treated with the shave care composition.

Derivatives of salicylic acid include, but are not limited to, any compounds wherein the CH3 groups are individually or in combination replaced by amides, esters, amino groups, alkyls, and alcohol esters. Tautomers of salicylic acid are the isomers of salicylic acid which can change into one another with ease so that they ordinarily exist in equilibrium. Thus, tautomers of salicylic acid can be described as having the chemical formula C7H6O3 and generally having a similar structure to salicylic acid.

The compositions of the present invention may include from about 0.001% to about 5%, alternatively from about 0.01% to about 2%, and alternatively from about 0.1% to about 1%, of alpha- or beta-hydroxy acids, and derivatives, salts, isomers and tautomers thereof. Non-limiting examples of alpha- and beta-hydroxy acids include alpha-hydroxybutyric acid, alpha-hydroxyisobutyric acid, alpha-hydroxyisocaproic acid, alpha-hydroxyisovaleric, atrolactic acid, beta-hydroxybutyric acid, beta-phenyl lactic acid, beta-phenylpyruvic acid, citric acid ethyl pyruvate, galacturonic acid, glucoheptonic acid, glucoheptono 1,4-lactone, gluconic acid, gluconolactone glucuronic acid, glucuronolactone, glycolic acid, isopropyl pyruvate, lactic acid, malic acid, mandelic acid, methyl pyruvate, mucic acid, pyruvic acid, saccharic acid, saccharic acid 1,4-lactone, tartaric acid and tartronic acid, and mixtures thereof.

Opacifiers may be added to the shave care composition of the present invention. Opacifiers may be either inorganic or organic compounds. Inorganic opacifiers include, for example, titanium dioxide, zinc oxide, talc, mica or coated mica (with oxides of titanium, tin, or iron or bismuth oxychloride), magnesium aluminum silicate, bismuth oxychloride, or other minerals. These compounds can be added as powders, dispersions, or complexes. Organic opacifiers include, for example, opaque emulsions (e.g., containing Styrene/PVP copolymer, vinyl polymers, or latexes), metal salts of amines containing 14-20 carbon atoms per molecule, alkanolamides containing 14-20 carbon atoms per molecule, organic alcohols containing 14-20 carbon atoms per molecule, insoluble salts of stearic acid, glycol mono- or distearates, propylene glycol and glycerol monostearates and palmitates. Combinations of these opacifiers can also be used. The opacifying additive is typically included in an amount of about 1 to about 6%, preferably about 2 to about 5%, by weight of the composition.

EXAMPLES

The following examples are provided to further illustrate exemplary shave care composition of the present invention.

TABLE 1*

| Ingredient | Ex. 1 | Ex. 2 | Ex. 3 | Ex. 4 | Ex. 5 |
|---|---|---|---|---|---|
| Phase A | | | | | |
| Water | 8.00% | 8.00% | 9.00% | 8.00% | 9.55% |
| Brij 35 (Laureth-23) | 2.00% | 2.00% | 2.20% | 2.00% | 1.50% |
| Plantaren 2000 N UP (Decyl Glucoside) | — | — | — | — | 0.50% |
| Phase B | | | | | |
| Xiameter PMX-200 Silicone Fluid, 30,000 cst (Dimethicone) | — | — | — | — | 3.00% |
| Petrolatum White | 12.00% | 12.00% | 4.00% | 12.00% | 10.00% |
| Wickenol 111 (Isopropyl Palmitate) | 3.00% | 3.00% | 1.00% | 3.00% | 1.40% |
| Petrolatum (G2218) | — | — | — | — | — |
| Hydrobrite 1000 (Mineral Oil) | — | — | — | — | — |
| Phase C | | | | | |
| Water | 59.81% | 58.11% | 69.11% | 59.21% | 60.46% |
| Brij 35 (Laureth-23) | 4.40% | 4.40% | 4.40% | 4.40% | 3.50% |
| Plantaren 2000 N UP (Decyl Glucoside) | — | — | — | — | 0.90% |
| Glycerin | 5.00% | 5.00% | 5.00% | 5.00% | 5.00% |
| Natrosol 250 HHR (Hydroxyethylcellulose) | 0.50% | 0.50% | 0.50% | 0.50% | 0.50% |
| Polyox WSR N-12K (PEG-23M) | — | — | — | — | — |
| PEG-90M (Polyox Wsr-301) | 0.20% | 0.20% | 0.20% | 0.20% | 0.20% |
| Sepigel 305 (Polyacrylamide & C13-14 Isoparaffin & Laureth-7) | 1.60% | 1.60% | — | 1.60% | — |
| Carbomer (Carbopol Ultrez 10) | — | — | 0.35% | — | 0.35% |
| Sodium Hydroxide (50% Solution) | — | — | 0.85% | — | 0.85% |
| Phase D | | | | | |
| Fragrance | 2.50% | 2.50% | 2.50% | 2.50% | 0.80% |
| Menthol | — | 0.50% | — | 0.50% | 0.30% |
| Menthyl Lactate | — | 1.20% | — | — | 0.20% |
| N-[4-(Cyanomethyl)phenyl]-2-isopropyl-5-methylcyclohexanecarboxamide ‡ | — | — | — | 0.10% | — |
| Iso E Super (Tetramethyl Acetyloctahydronaphthalenes) | — | — | — | — | — |
| Disodium EDTA | 0.10% | 0.10% | 0.10% | 0.10% | 0.10% |
| Glydant 55 (DMDM Hydantoin) | 0.30% | 0.30% | 0.20% | 0.30% | 0.30% |
| Glycacil L (Iodopropynyl Butylcarbamate) | 0.09% | 0.09% | 0.09% | 0.09% | 0.09% |
| Phenoxetol (Phenoxyethanol) | 0.50% | 0.50% | 0.50% | 0.50% | 0.50% |
| TOTAL | 100% | 100% | 100% | 100% | 100% |

TABLE 2*

| Ingredient | Ex. 6 | Ex. 7 | Ex. 8 | Ex. 9 | Ex. 10 | Ex. 11 |
|---|---|---|---|---|---|---|
| Phase A | | | | | | |
| Water | 16.00% | 5.25% | 5.25% | 7.20% | 16.00% | 12.10% |
| Brij 35 (Laureth-23) | 3.50% | 1.30% | 1.30% | 1.80% | 4.00% | 4.00% |
| Plantaren 2000 N UP (Decyl Glucoside) | 0.50% | — | — | — | — | — |
| Phase B | | | | | | |
| Xiameter PMX-200 Silicone Fluid, 30,000 cst (Dimethicone) | — | — | — | — | — | 4.00% |
| Petrolatum White | 24.00% | — | 10.00% | — | — | — |
| Wickenol 111 (Isopropyl Palmitate) | 8.40% | — | 2.00% | — | — | — |
| Petrolatum (G2218) | — | 7.00% | — | 12.00% | 21.00% | 24.00% |
| Hydrobrite 1000 (Mineral Oil) | — | 3.00% | — | 1.60% | 9.00% | 6.00% |
| Phase C | | | | | | |
| Water | 29.36% | 68.56% | 68.18% | 62.81% | 36.81% | 34.91% |
| Brij 35 (Laureth-23) | 2.60% | 4.10% | 3.20% | 4.30% | 4.40% | 4.40% |
| Plantaren 2000 N UP (Decyl Glucoside) | 0.50% | — | — | — | — | — |
| Glycerin | 10.00% | 5.00% | 5.00% | 6.50% | 5.00% | 7.00% |
| Natrosol 250 HHR (Hydroxyethylcellulose) | 0.25% | 0.50% | 0.50% | — | 0.50% | 0.50% |
| Polyox WSR N-12K (PEG-23M) | 0.20% | — | — | — | — | — |
| PEG-90M (Polyox Wsr-301) | 0.20% | 0.20% | 0.20% | 0.20% | 0.20% | 0.20% |
| Sepigel 305 (Polyacrylamide & C13-14 Isoparaffin & Laureth-7) | — | 1.60% | — | 1.70% | 1.30% | 1.20% |
| Carbomer (Carbopol Ultrez 10) | 0.30% | — | 0.35% | — | — | — |
| Sodium Hydroxide (50% Solution) | 0.80% | — | 0.85% | — | — | — |
| Phase D | | | | | | |
| Fragrance | 2.50% | 2.50% | 1.50% | 0.80% | 0.80% | 0.80% |
| Menthol | — | — | 0.40% | 0.30% | — | — |
| Menthyl Lactate | — | — | 0.45% | — | — | — |
| N-[4-(Cyanomethyl)phenyl]-2-isopropyl-5-methylcyclohexanecarboxamide ‡ | — | — | 0.02% | — | — | — |
| Iso E Super (Tetramethyl Acetyloctahydronaphthalenes) | — | — | — | 0.05% | — | — |
| Glydant Plus (DMDM Hydantoin & Iodopropynyl Butylcarbamate & Water) | — | — | 0.20% | — | — | — |
| Disodium EDTA | 0.10% | 0.10% | 0.10% | 0.10% | 0.10% | 0.05% |
| Glydant 55 (DMDM Hydantoin) | 0.20% | 0.30% | — | 0.30% | 0.30% | 0.30% |
| Glycacil L (Iodopropynyl Butylcarbamate) | 0.09% | 0.09% | — | 0.09% | 0.09% | 0.04% |
| Phenoxetol (Phenoxyethanol) | 0.50% | 0.50% | 0.50% | 0.25% | 0.50% | 0.50% |
| TOTAL | 100% | 100% | 100% | 100% | 100% | 100% |

TABLE 3*

| Ingredient | Ex. 12 | Ex. 13 | Ex. 14 | Ex. 15 | Ex. 16 | Ex. 17 | Ex. 18 |
|---|---|---|---|---|---|---|---|
| Phase A | | | | | | | |
| Water | 8.00% | 25.00% | 25.00% | 25.00% | 8.00% | 25.00% | 16.00% |
| Brij 35 (Laureth-23) | 2.00% | 6.40% | 6.40% | 4.00% | 1.30% | 6.40% | 4.00% |
| Plantaren 2000 N UP (Decyl Glucoside) | — | — | — | 2.30% | — | — | — |
| Phase B | | | | | | | |
| Xiameter PMX-200 Silicone Fluid, 30,000 cst (Dimethicone) | — | — | — | 2.00% | — | — | — |
| Petrolatum White | 12.00% | — | — | — | — | — | 24.00% |
| Wickenol 111 (Isopropyl Palmitate) | 3.00% | — | 5.00% | — | 2.00% | 5.00% | 3.00% |
| Petrolatum (G2218) | — | 45.00% | 40.00% | 45.00% | 8.00% | 40.00% | — |
| Hydrobrite 1000 (Mineral Oil) | — | 5.00% | 5.00% | 5.00% | — | 5.00% | 3.00% |

TABLE 3*-continued

| Ingredient | Ex. 12 | Ex. 13 | Ex. 14 | Ex. 15 | Ex. 16 | Ex. 17 | Ex. 18 |
|---|---|---|---|---|---|---|---|
| Phase C | | | | | | | |
| Water | 59.41% | 7.10% | 5.50% | 6.06% | 66.25% | 5.50% | 36.81% |
| Brij 35 (Laureth-23) | 4.40% | 3.10% | 3.10% | 2.00% | 4.50% | 3.10% | 4.40% |
| Plantaren 2000 N UP (Decyl Glucoside) | — | — | — | 1.70% | — | — | — |
| Glycerin | 5.00% | 5.00% | 6.50% | 3.00% | 5.00% | 6.50% | 5.00% |
| Natrosol 250 HHR (Hydroxyethylcellulose) | 0.50% | 0.25% | 0.25% | 0.50% | 0.25% | 0.25% | 0.50% |
| Polyox WSR N-12K (PEG-23M) | 0.40% | — | 0.40% | 0.10% | — | 0.40% | — |
| PEG-90M (Polyox Wsr-301) | 0.20% | 0.20% | 0.20% | 0.10% | 0.20% | 0.20% | 0.20% |
| Sepigel 305 (Polyacrylamide & C13-14 Isoparaffin & Laureth-7) | 1.60% | 1.10% | 1.10% | — | 1.10% | 1.10% | 1.30% |
| Carbomer (Carbopol Ultrez 10) | — | — | — | 0.25% | — | — | — |
| Sodium Hydroxide (50% Solution) | — | — | — | 0.70% | — | — | — |
| Phase D | | | | | | | |
| Fragrance | 2.50% | 0.80% | 1.00% | 1.00% | 2.50% | 1.00% | 0.80% |
| Menthol | — | 0.15% | — | 0.30% | — | — | — |
| Menthyl Lactate | — | — | — | 0.20% | — | — | — |
| N-[4-(Cyanomethyl)phenyl]-2-isopropyl-5-methylcyclohexanecarboxamide ‡ | — | — | — | — | — | — | — |
| Iso E Super (Tetramethyl Acetyloctahydronaphthalenes) | — | — | — | — | — | — | — |
| Glydant Plus (DMDM Hydantoin & Iodopropynyl Butylcarbamate & Water) | — | — | 0.20% | — | — | 0.20% | — |
| Disodium EDTA | 0.10% | 0.05% | 0.10% | 0.05% | 0.05% | 0.10% | 0.10% |
| Glydant 55 (DMDM Hydantoin) | 0.30% | 0.30% | — | 0.20% | 0.30% | — | 0.30% |
| Glycacil L (Iodopropynyl Butylcarbamate) | 0.09% | 0.05% | — | 0.04% | 0.05% | — | 0.09% |
| Phenoxetol (Phenoxyethanol) | 0.50% | 0.50% | 0.25% | 0.50% | 0.50% | 0.25% | 0.50% |
| TOTAL | 100% | 100% | 100% | 100% | 100% | 100% | 100% |

*Percentages in Tables 1-3 on a weight by weight basis.
‡ N-[4-(Cyanomethyl)phenyl]-2-isopropyl-5-methylcyclohexanecarboxamide available as Evercool G-180 from Givaudan SA.

The above Examples in Tables 1-3 are made according to the method below.

1. Weigh out water from Phase C into a vessel sufficient to hold the entire batch and heat to above 60 C while mixing. Add remaining materials while allowing for sufficient mixing, melting, dispersion and/or incorporation between each addition to form a uniform mixture.
2. Weigh out the water from Phase A into a separate vessel and heat contents to above 60 C while mixing.
3. Add remaining materials from Phase A and mix until fully melted and dissolved.
4. Weigh out the materials from Phase B into a separate vessel and heat contents to above 60 C while mixing.
5. Apply high-shear to Phase A using homogenizer/mill while slowly adding the contents of Phase B to the vessel containing Phase A. Continue homogenization after the addition has been completed.
6. Stop homogenization of the combined Phases A and B, and add mixture to the vessel containing Phase C.
7. Adjust pH for formulas containing Carbomer using Sodium Hydroxide.
8. Begin cooling batch to below 45 C while continuing to mix
9. Once below 45 C, add the materials in Phase D in succession and continue mixing
10. Cool to below 30 C and QS with water For product with menthol, menthyl lactate or Evercool G-180, dissolve these materials s in fragrance in a separate vessel and add to the final batch during other Phase D additions.

2. Rheological Characteristics

The compositions herein can be characterized as shear-thinning fluids which can be further described using a Power-Law model expressed as $$\mu_{eff} = K(\dot{\gamma})^{n-1}$$

where $\mu_{eff}$ is the effective viscosity in pascal-seconds (Pa·s) at a given shear rate, K is Consistency in pascal-seconds (Pa·s), $\dot{\gamma}$ is the shear rate in reciprocal seconds (s$^{-1}$), and n is the Power-Law Index in dimensionless units. Such fluid behavior and characterization is well known in the art and can be further found in *Rheology, Principles, Measurements, and Applications* by Christopher Macosko (Wiley-VCH, 1994). The shear-thinning nature of fluids is described by the Power-Law model where the Power-Law Index is less than 1. The compositions of the present invention exhibit a Power-Law Index less than about 0.5 and a Power-Law Consistency of less than about 50 Pa·s, preferably less than about 48 Pa·s, more preferably less than about 45 Pa·s, most preferably less than about 38 Pa·s. Further, the compositions of the present invention exhibit a Power-Law Index less than about 0.5 and a Power-Law Consistency of greater than about 20 Pa·s, preferably greater than about 23 Pa·s, more preferably greater than about 25 Pa·s, most preferably greater than about 30 Pa·s. One preferred embodiment exhibits a Power-Law Index of about 0.36 and a Power-Law Consistency of about 32 Pa·s.

The flow rheology according to the Power-Law Model is indicative that the composition will perform as intended within the present invention of a liquid dispensing razor. Compositions with a shear-thinning nature and a Power-Law Consistency less than the aforementioned preferred minimum values will flow out of the razor during horizontal storage or drip off of the razor and not get delivered to the skin during use of the product or lead to dispersed phase instability and separation of the composition. Products with a shear-thinning nature and a Power-Law Consistency greater than the preferred values will not easily dispense via the pump or will not readily refill the pump from the reservoir or will not sufficiently evacuate the entire contents of the reservoir during use. In addition, products with a shear-thinning nature and a Power-Law Consistency greater than the preferred values will not easily spread across the razor to provide the desired distribution of product for protection of the skin during multiple strokes with the razor.

3. Rheological Characterization

Flow rheology measurements are conducted using an AR2000 Rheometer (TA Instruments, Rheology Advantage Instrument Control AR V5.7.0 software) and standard-size DIN/conical concentric cylinder geometry (Aluminum, Stator inner radius=15.00 mm, Rotor outer radius=14.00 mm, Cylinder immersed height=42.00, Gap=5920 micrometers). Samples are loaded by dispensing known weight (16 g) onto instrument while taking care to not introduce air bubbles into the sample. After sample loading, a flow rheology procedure is completed according to the following procedure: 1. Temperature equilibration to 25° C., 2. Pre-shearing at 10 $s^{-1}$ for 60 seconds to normalize loading effects, followed by 5 minute equilibration with no shearing, 3. Continuous shear rate ramp from 0.001 to 4355.0 $s^{-1}$ over 5 minute time period with 10 data points collected per shear rate decade). Flow rheology is exported and analyzed using Rheology Data Fitting 2.1.3 (software developed by Procter & Gamble, Fabric & Home Care, Process & Equipment Modeling & Simulation using Python programming language) and data points greater than 0.01 $s^{-1}$ are fitted to the Power-Law model expressed earlier.

4. Liquid Dispensing Razor

The composition dispensing device of the present invention can be any such device which allows the present composition to be dispensed therefrom during the hair removal process. Examples of many types of composition dispensing devices are known. In one embodiment, the composition dispensing device is a liquid dispensing razor comprising one or more safety razors.

In one embodiment, the liquid dispensing razor comprises a handle and a razor cartridge including a housing with an aperture, a cartridge connecting structure, and a fluid dispensing member disposed in the cartridge connecting member. The handle has a length that extends from a proximal end to a distal end. The handle includes a cavity for housing a reservoir of fluid disposed within the handle near the distal end, a connector port disposed at the proximal end and a manually-actuated pump located along the length of the handle between the reservoir and the connector port.

The connector port comprises a connector port supply end having an opening and a connector port discharge end having an opening with a connector port flowpath therebetween. The connector port flowpath includes a converging cross-section, such that the cross-section of the connector port flowpath decreases from the supply end opening to the discharge end opening. Alternatively, the connector port comprises a Y-shaped flowpath where the connector port supply end has one opening and the connector port discharge end has two openings with the connector port Y-shaped flowpath therebetween. For this embodiment, the connector port flowpath comprises a supply end flowpath leading to two discharge end flowpaths. The supply end flowpath and two discharge end flowpaths include converging cross-sections, such that the cross-sections of each of the flowpaths decreases in the direction of flow.

The razor cartridge includes a housing having a top portion, bottom portion, front surface, and rear surface; and a cartridge connecting structure attached to the rear surface of the housing. At least one blade is positioned between the top portion and the bottom portion of the housing and an aperture located between the top portion and the bottom portion extends from the rear surface to the front surface. The razor cartridge is pivotally connected to the cartridge connecting structure and may be removably connected to the connecting structure. Additionally, the razor cartridge may include a guard as well as an elastomeric member disposed on the guard.

A fluid dispensing member is joined to the cartridge connecting structure. The fluid dispensing member includes at least one, preferably two flowpaths, wherein each flowpath has a fluid dispensing member opening at a fluid dispensing member supply end and two fluid dispensing member openings at a fluid dispensing member discharge end. The fluid dispensing member flowpaths converge from the fluid dispensing member supply ends to the fluid dispensing member discharge ends such that the cross-sections of the flowpaths decrease from the supply end openings to the discharge end openings. The fluid dispensing member discharge end openings extend to or adjacent to the aperture in the housing allowing for direct contact to a user during shaving. The fluid dispensing member is in fluid communication with the reservoir and pump via the connector port when the cartridge connecting structure engages the proximal end of the handle.

A hollow space or cavity may be interposed between the connector port discharge end opening and the dispensing member supply end openings for the connector port configuration having the single converging flowpath design. The hollow space or cavity may be formed as part of the cartridge connecting structure. For the connector port configuration including the Y-shaped flowpath, the two discharge ends of the connector port flowpath may interface directly with the fluid dispensing member supply end openings.

In an another embodiment, razor cartridge includes a housing, a cap, and at least one blade mounted to the housing. The blade has a blade edge in front of the cap. A guard in front of the blade. The guard defines an elongated recess or trough having an overall width extending parallel to the blade that is 70% to 100% of an overall width of the guard. The elongated recess is in fluid communication with the fluid dispensing member discharge end opening via the apertures in the cartridge housing and may be filled with fluid pumped from the reservoir.

In order to accommodate the flow of fluid for the entire pivot range of the cartridge, the fluid dispensing member discharge end openings are flared. The external surfaces of the fluid dispensing member adjacent the discharge end openings are curved concave toward the opening while the internal surfaces of the openings form a beveled edge. The flared openings interface with the apertures in the housing. An elongated recess or trough in the guard that is in fluid communication with the apertures can provide an even distribution of fluid along the length of the blades. Microcombs in the guard between the trough and the blades can evenly distribute fluid across the blade span.

A pump is disposed between the reservoir and the connector port. The pump can comprise a resilient tube interposed between first and second connectors, where the first and second connectors include first and second valves, respectively. The first connector attaches to the reservoir and the second connector attaches to the connector port opening. The resilient tube has a neutral position with both valves closed and a second position with one valve open and one valve closed.

The fluid is stored in a reservoir disposed in a cavity at the distal end of the handle opposite the connector port. The reservoir is replaceable and comprises an outer container enclosing a collapsible inner container and includes a fluid outlet adapted to allow fluid to exit both the collapsible reservoir and the container. An orifice disposed in the outer container is adapted to allow air to flow in or out of the container. The fluid outlet is in fluid communication with the pump which sucks fluid out of the collapsible reservoir. The fluid outlet may include a frangible seal which is penetrated by a piercer on the end of the first connector during connection of the reservoir to the pump. The reservoir can be disposed at the distal end of the handle and can comprise an exposed container or bottle or covered by an end cap.

Figure 2:
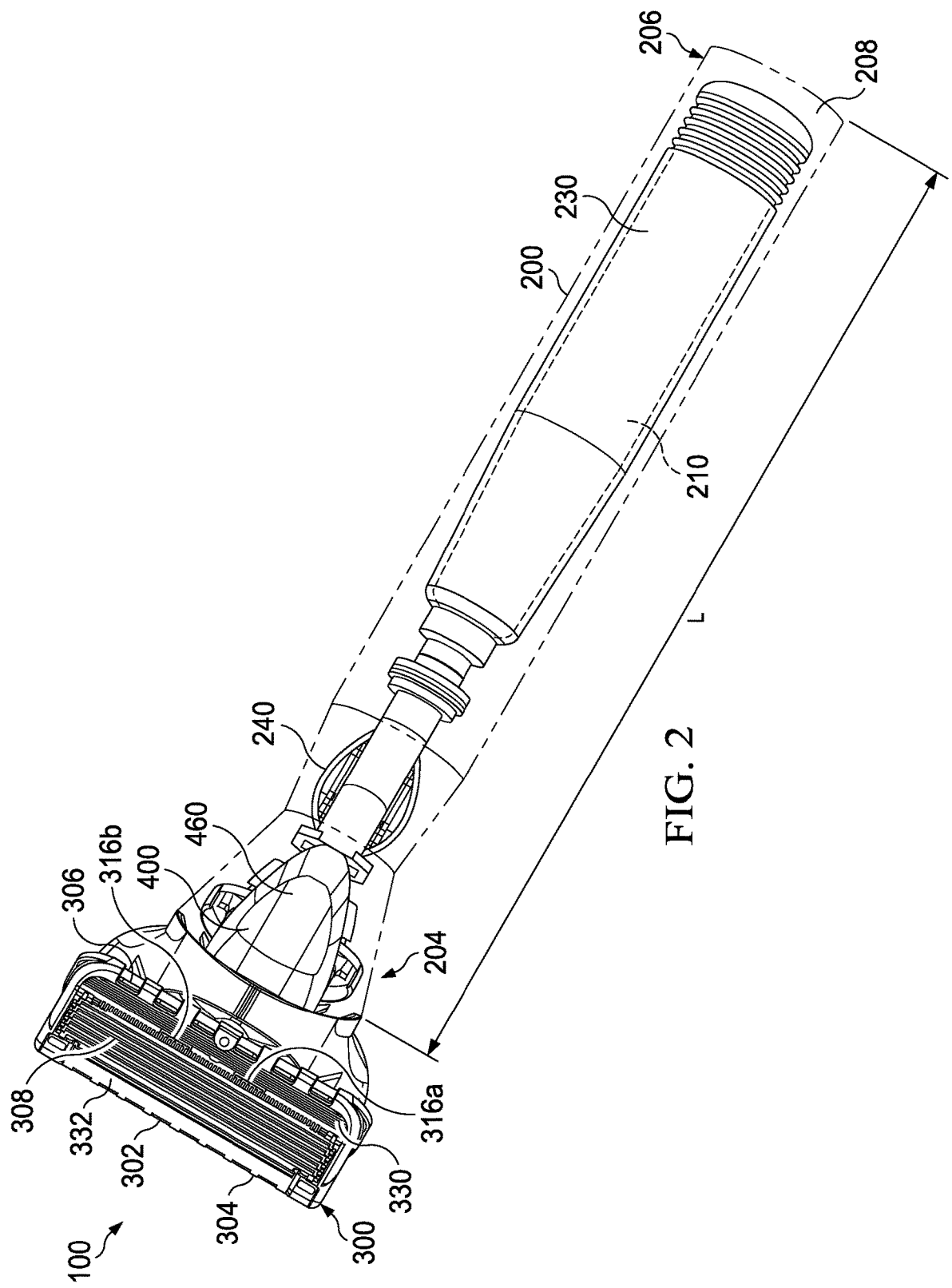
FIG. 2 is a bottom view of a wet shaving razor of the present invention.
Figure 3:
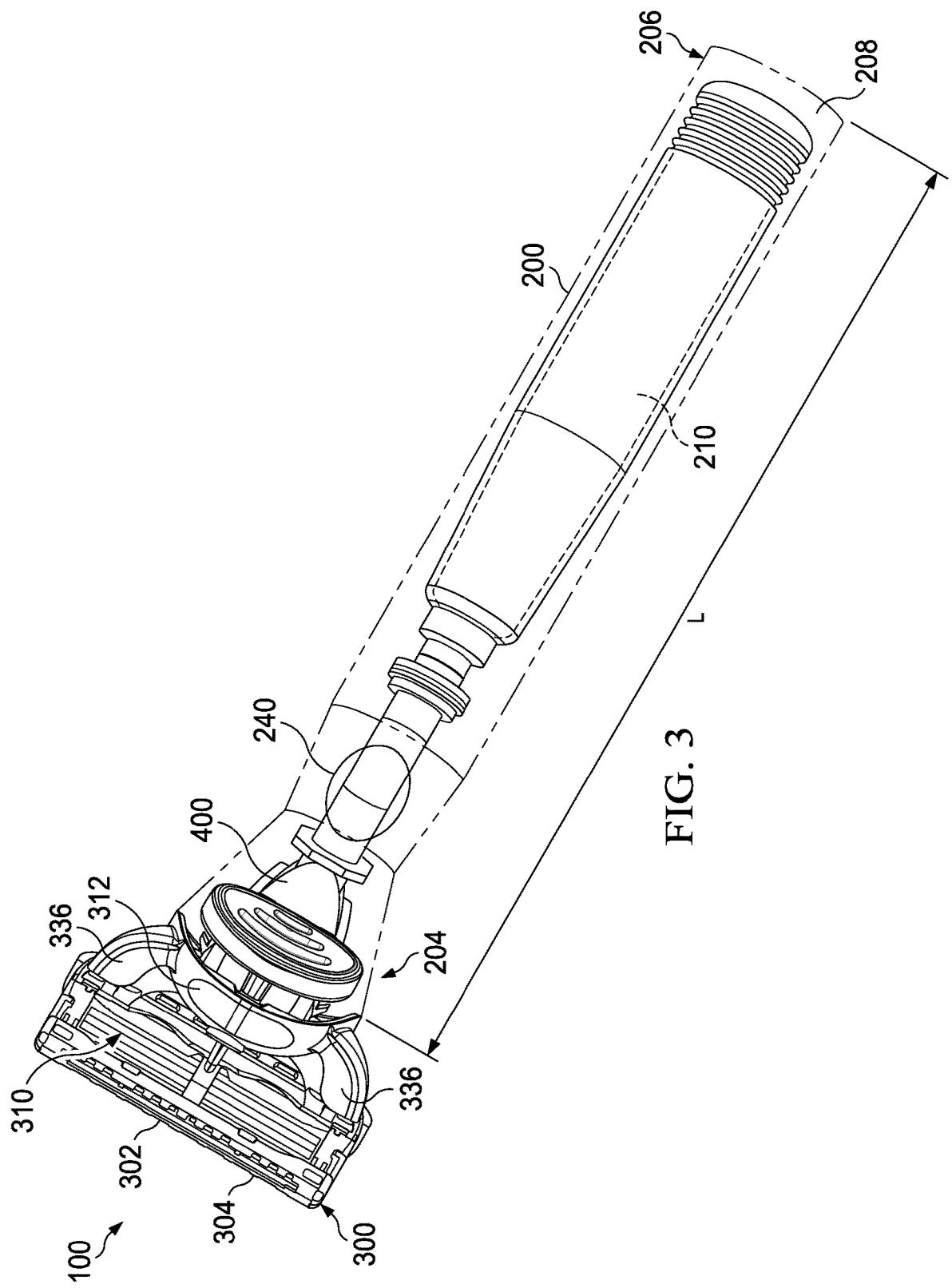
FIG. 3 is a top view of a wet shaving razor of the present invention.

FIGS. 1-3 show a liquid dispensing wet shaving razor (100) for dispensing a fluid during shaving that includes a handle (200) and a razor cartridge (300). The handle (200) has a length (L) that extends from a proximal end (204) to a distal end (206). The handle also includes a cavity (208) for housing a reservoir (230) disposed within the handle (200) and a manually-actuated pump (240) located along the length (L) of the handle (200). The pump assembly (240) is adapted to displace the fluid from the reservoir (230) to a connector port (400) at the proximal end (204) of the handle (200).

Referring to FIGS. 1-3, the razor cartridge (300) includes a housing (302) having a top portion (304), bottom portion (306), front surface (308), and rear surface (310). At least one blade (314) is positioned between the top portion (304) and the bottom portion (306). The razor cartridge (300) may also include multiple blades. For example, U.S. Pat. No. 7,168,173 generally describes a Fusion® razor that is commercially available from The Gillette Company which includes a razor cartridge with multiple blades. Additionally, an aperture (316) is located between the top portion (304) and the bottom portion (306) such that the aperture (316) extends from the rear surface (310) to the front surface (308). In an embodiment, the housing (302) may also contain clips that are useful for retaining and maintaining the stability of the blades before, during, and after use of the razor.

The cartridge (300) attaches to the rear surface (310) of the housing (302) by a cartridge connecting structure (312). The cartridge connecting structure (312) includes two arms (336) that extend to provide pivotal support of the housing (302). The cartridge is able to pivot about a predetermined axis located beneath the guard surface (330). (Apertures 316a and 316b are preferably located at or near the pivot axis fully described below).

The razor cartridge (300) may also include a guard (330) and/or lubricating strip (332) on the front surface (308) located between the top portion (304) and bottom portion (306) of the housing (302). The guard (330) is useful for stretching the skin's surface immediately prior to engagement with the blade or a first blade (when more than one blade is present). This guard (330) may typically comprise an elastomeric member to allow for an engagement that is comfortable to a user. U.S. Pat. No. 7,168,173 discloses a suitable razor cartridge and elastomeric material without the apertures. The elastomeric material can be selected as desired. Typically, the elastomeric material used is a block copolymer (or other suitable materials), e.g., having a durometer between 28 and 60 Shore A.

Figure 5:
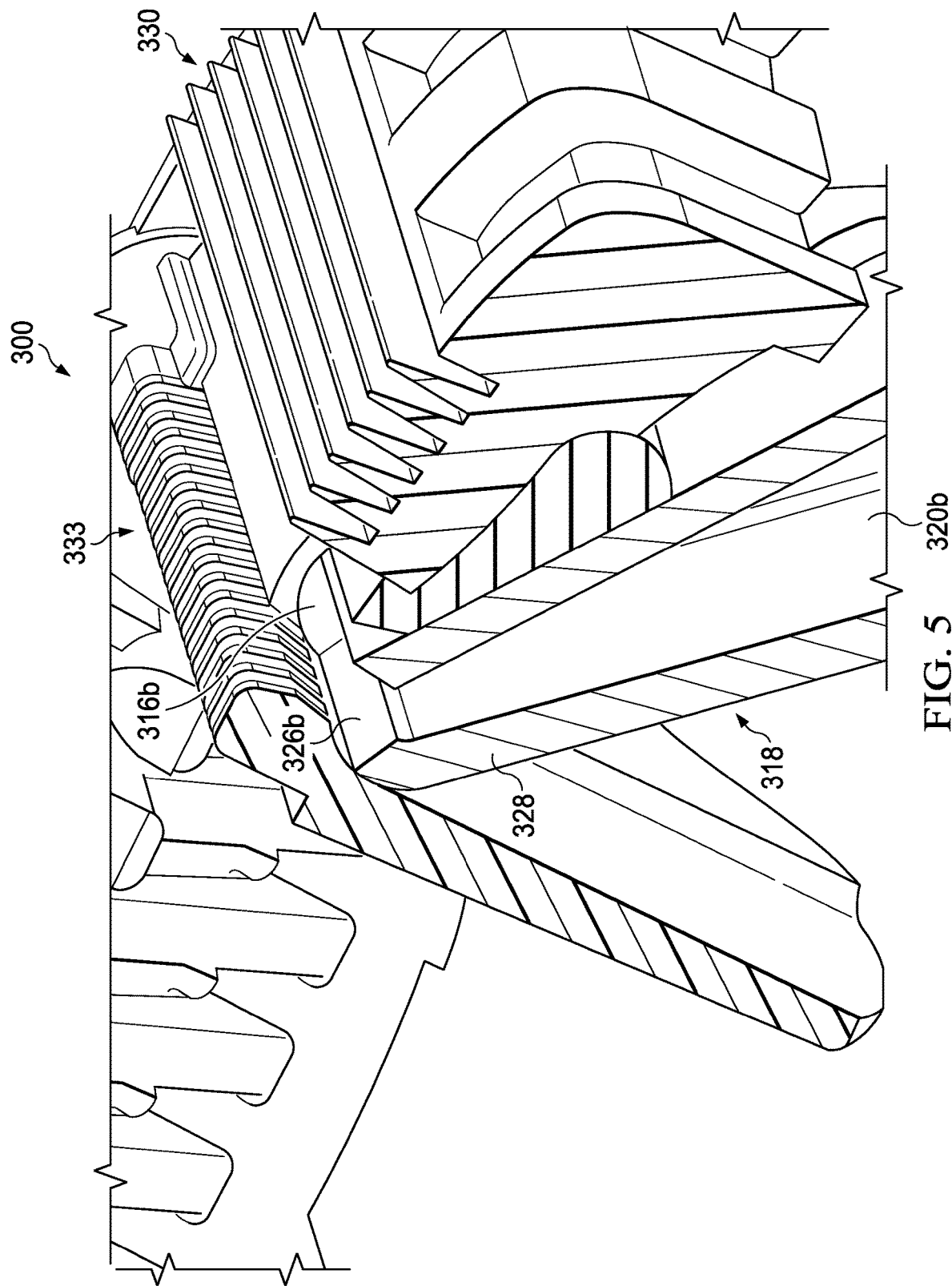
FIG. 5 is a perspective view of a cross-section of the razor cartridge of the wet shaving razor shown in FIGS. 1-3.

The razor cartridge may also include a micro comb (333) Shown in FIG. 5 and disclosed in U.S. Pat. No. 8,209,867. The micro comb (333) includes a plurality of projections defining a plurality of open slots extending generally perpendicular to the blade edge. The open slots have a minimum dimension to allow free passage of hair to the blade edge and a maximum dimension which prevents skin bulge between the slots. The micro combs are disposed between the blade edge and the apertures (316a and 316b) in the housing and serve as flow channels providing an even distribution of fluid in front of the blade edge.

The lubricating strip, on the other hand, provides an additional treatment to the skin after contact between the fluid and the skin has occurred. The lubricating strip may contain the same or additional skin ingredients to those that are present in the fluid. Suitable lubricating strips are disclosed in U.S. Pat. Nos. 7,069,658, 6,944,952, 6,594,904, 6,182,365, D424,745, 6,185,822, 6,298,558 and 5,113,585. The lubricating strips may be located anywhere on the cartridge and contains electrolyte that is released to the skin which further facilitates the spreading of the polymer thickened/suspended ingredients. The electrolyte can be charged polymers, salts, surfactants or mixtures therein.

The cartridge connecting structure (312) may be releasably attached to the handle (200), as disclosed in U.S. Pat. Nos. D533,684, 5,918,369, and 7,168,173. This disengagement of these two components allows for replacement of razor cartridges as the continued use of such cartridges causes blade dulling. Thus, such cartridges are replaceable and disposable at will by the user.

The razor cartridge 300 comprises a pivot axis about which the cartridge housing 302 is mounted to the cartridge connecting structure (312). In one embodiment, the one or more apertures 316a and 316b in the front surface 308 of the cartridge are positioned at or close to the pivot axis. The one or more aperture(s) allow fluid to be discharged directly to the skin at or near the predetermined pivot axis. Non-limiting examples of devices having similar placement of the discharge positions of fluid are available in U.S. Pat. No. 6,789,321. In one embodiment the device comprises a plurality of orifice(s) wherein one or more of said plurality of orifice(s) are positioned at or close to the pivot axis. The one or more of orifice(s) can generally form a line extending for a portion of said pivot axis. The device could also have just one orifice which has a generally elongated shape extending sideways towards the lateral ends of the razor cartridge, extending for a portion of the pivot axis. By providing one or more orifice(s) positioned along a portion of any fluid dispensed at the pivot axis would have a greater chance of forming a thin but wide ribbon of the fluid. Non-limiting examples of suitable orifices are provided herein and also available in U.S. Published Patent Application US 20110219621 A1.

Fluid Dispensing Member

Figure 4A:
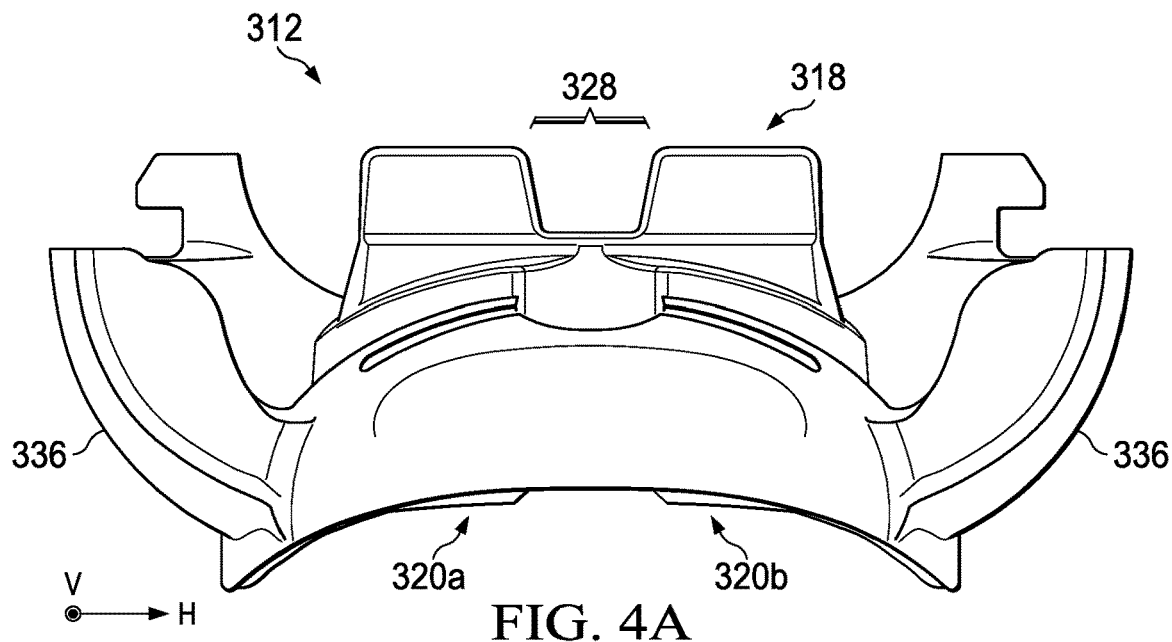
FIG. 4a is a top view of a razor cartridge connecting structure of the present invention.
Figure 4B:
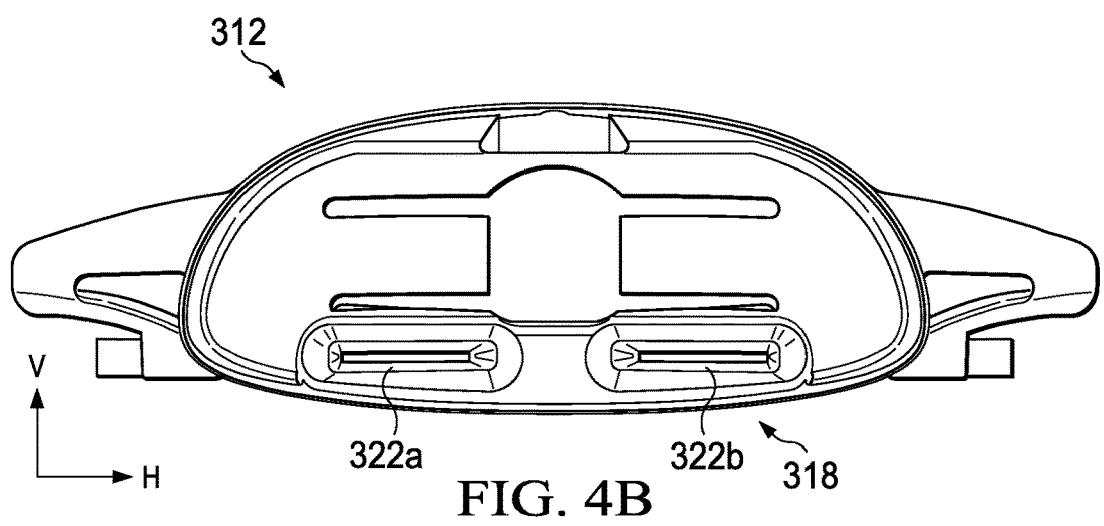
FIG. 4b is a rear view of a razor cartridge connecting structure of the present invention.
Figure 4C:
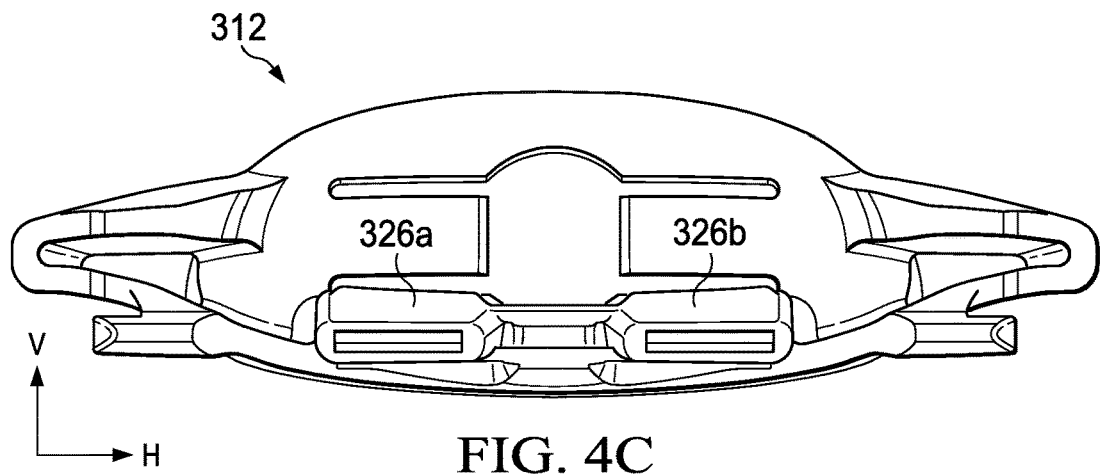
FIG. 4c is a front view of a razor cartridge connecting structure of the present invention.

The razor cartridge shown in FIGS. 4a-4c comprises a fluid dispensing member (318) joined to the cartridge connecting structure (312). The fluid dispensing member (318) includes two dispensing member flowpaths 320a and 320b with two dispensing member supply end openings 322a and 322b and two dispensing member discharge end openings 326a and 326b. The two fluid dispensing member supply end openings 322a and 322b are in fluid communication with the connector port discharge end opening(s) when the cartridge connecting structure engages the proximal end of the handle and the two dispensing member discharge end openings (326a and 326b) are in fluid communication with the apertures 316a and 316b in the housing 302. The dispensing member flowpaths (320a and 320b) converge from the dispensing member supply end openings (322a and 322b) to the dispensing member discharge end openings 326a and 326b such that the cross-sections of the dispensing member flowpaths (320a and 320b) decrease from the two dispensing member supply end openings (322a and 322b) to the two dispensing member discharge end openings (326a and 326b). The cross sections of the dispensing member flowpaths (320a and 320b) can decrease continuously from the supply end openings (322a and 322b) to the discharge end openings (326a and 326b). The cross sections may decrease in the horizontal direction H, vertical direction V or both. For instance, the cross sections of the flowpaths (320a and 320b) for the dispensing member 318 in the connecting structure (312) shown in FIGS. 4b and 4c, decrease in both the horizontal H and vertical directions V. Upon engaging the fluid dispensing member supply end openings 322a and 322b with the connector port discharge end opening(s), the fluid dispensing member (318) is in fluid communication with the pump (240) and actuation of the pump (240) displaces the fluid from the reservoir (230) in the cavity (208) through the apertures (316) to or adjacent to the front surface (308) of the housing (302).

If a clog or problem occurs in the flowpaths (320a) and (320b) and/or the razor cartridge (300), e.g., blades become dull, a user can simply replace the cartridge (300) and accompanying fluid dispensing member (318). The fluid dispensing member (318) may be integrally formed with the cartridge connecting structure (312). For example, the fluid dispensing member (318) may be molded and/or formed as a single assembly with the cartridge connecting structure (312).

The dispensing end (328) of the dispensing member (318) extends to or adjacent to the apertures 316a and 316b in the housing (302). In the partial view of the cartridge housing 302 and fluid dispensing member 318 dispensing end 328 shown in FIG. 5, the dispensing end (328) engagably mates with the razor cartridge (300) at the aperture (316b). To prevent the fluid from leaking while the razor (100) is not in use, any or all of the openings (e.g., 322a, 322b, 326a and 326b) may include a check valve, e.g., a slit valve, a duck valve, or other suitable valves.

As shown in FIG. 5, the fluid dispensing member (318) has discharge end openings (326a, 326b) at the dispensing end (328) and the razor cartridge (300) includes apertures (316a, 316b). Discharge end openings (326a and 326b) in the dispensing end (328) of the fluid dispensing member (318) can be beveled. As shown, edges of the discharge end openings (326a and 326b) are disposed at an angle relative to the openings to accommodate an entire pivot range of the razor cartridge 300. In this embodiment, the dispensing end (328) projects outwardly and extends into the plurality of apertures (316a, 316b) to or adjacent to the front surface (308). Upon engaging the supply end openings (322a and 322b) of the fluid dispensing member (318) with the connector port flowpath (425), the fluid dispensing member (318) is in fluid communication with the pump (240). Actuation of the pump (240) displaces the fluid (210) from the reservoir (230) through the apertures (316a, 316b) to or adjacent to the front surface (308) of the housing (302).

Connector Port

Figure 6A:
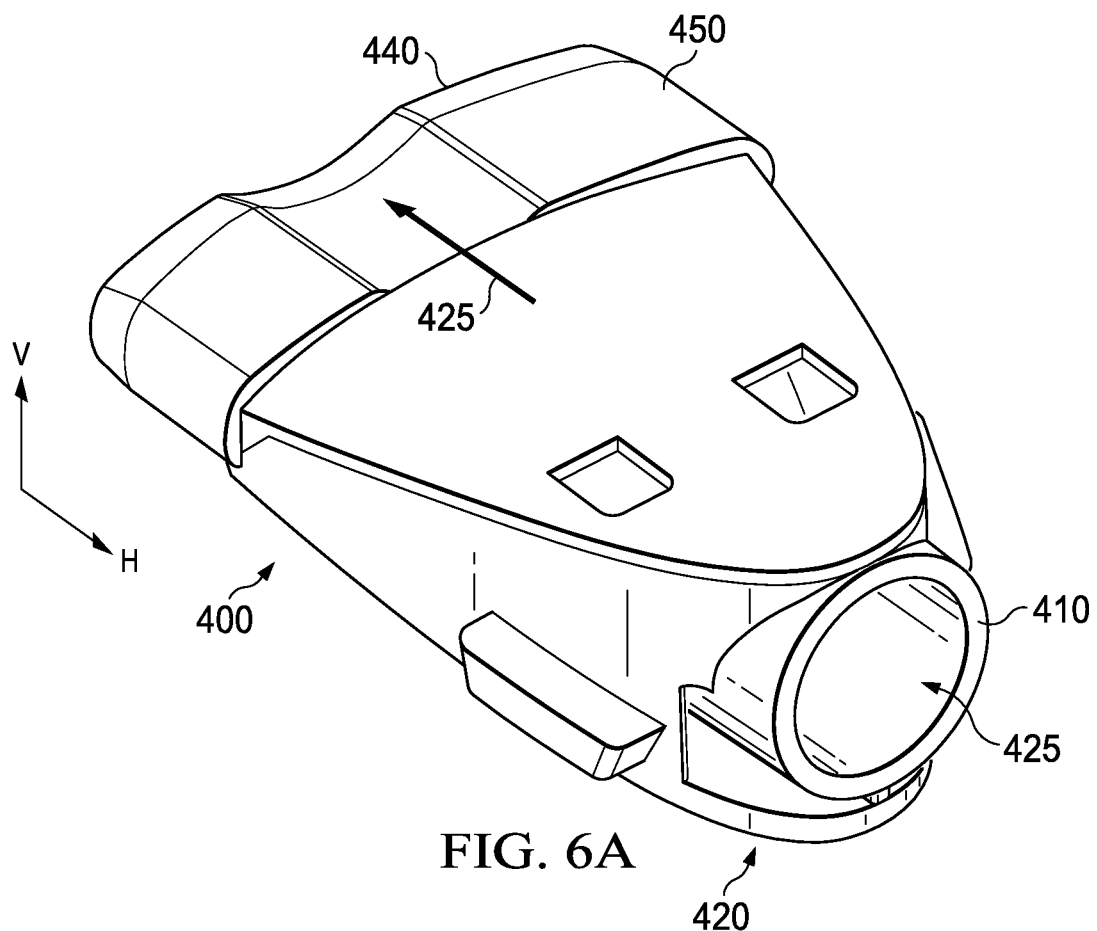
FIGS. 6a and 6b are perspective views of a connector port of the wet shaving razor shown in FIGS. 1-3.
Figure 6B:
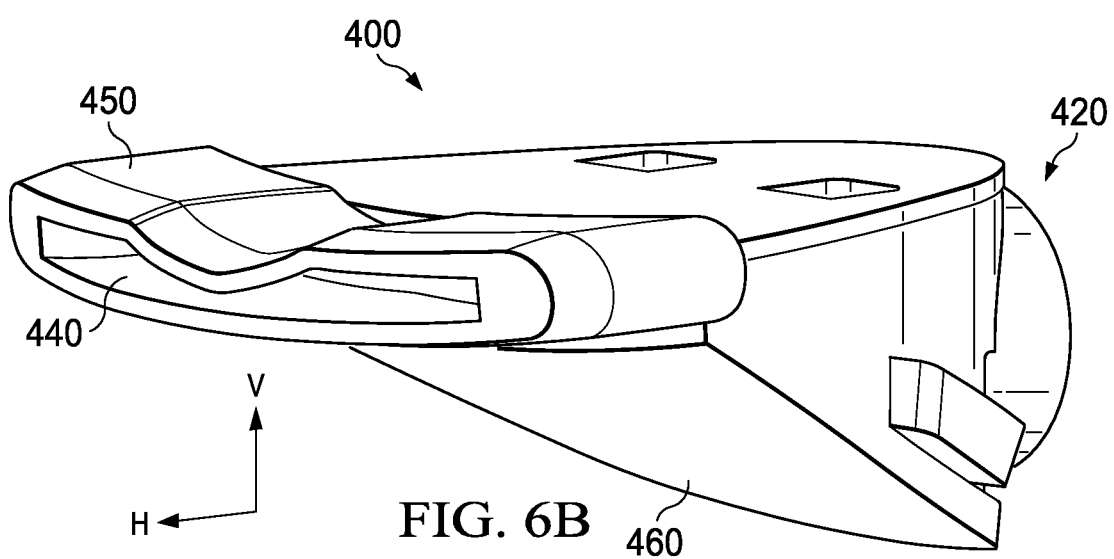

The connector port 400 shown in FIGS. 6a and 6b comprises a connector port supply end 420 having an opening 410 and a connector port discharge end (450) having an opening (440) with a connector port flowpath 425 therebetween. The connector port flowpath 425 includes a converging cross-section, such that the cross-section of the connector port flowpath contracts from the supply end opening 410 to the discharge end opening 440. The decrease in cross-section refers to the reduction in area as the flowpath progresses from the supply end opening 410 to the discharge end opening 440 along the flowpath. For the connector port shown in FIGS. 6a and 6b, the cross-sections may decrease in the horizontal direction H, vertical direction V or both. For instance, the cross-section of the flowpath (425) for the connector port (400) shown in FIGS. 6a and 6b, decreases in the vertical direction V.

In order to provide a visual indication of the fluid flowing though the razor assembly, the connector port 400 may include a transparent or translucent window providing a visual indication that the fluid is flowing through the connector port 400. The transparent or translucent window may be disposed on any portion of the connector port that is exposed. As shown in FIG. 2 and FIG. 6b the bottom portion 460 of the connector port 400 may comprise a transparent or translucent window that is exposed on the bottom portion of the liquid dispensing wet shaving razor (100).

Figure 7:
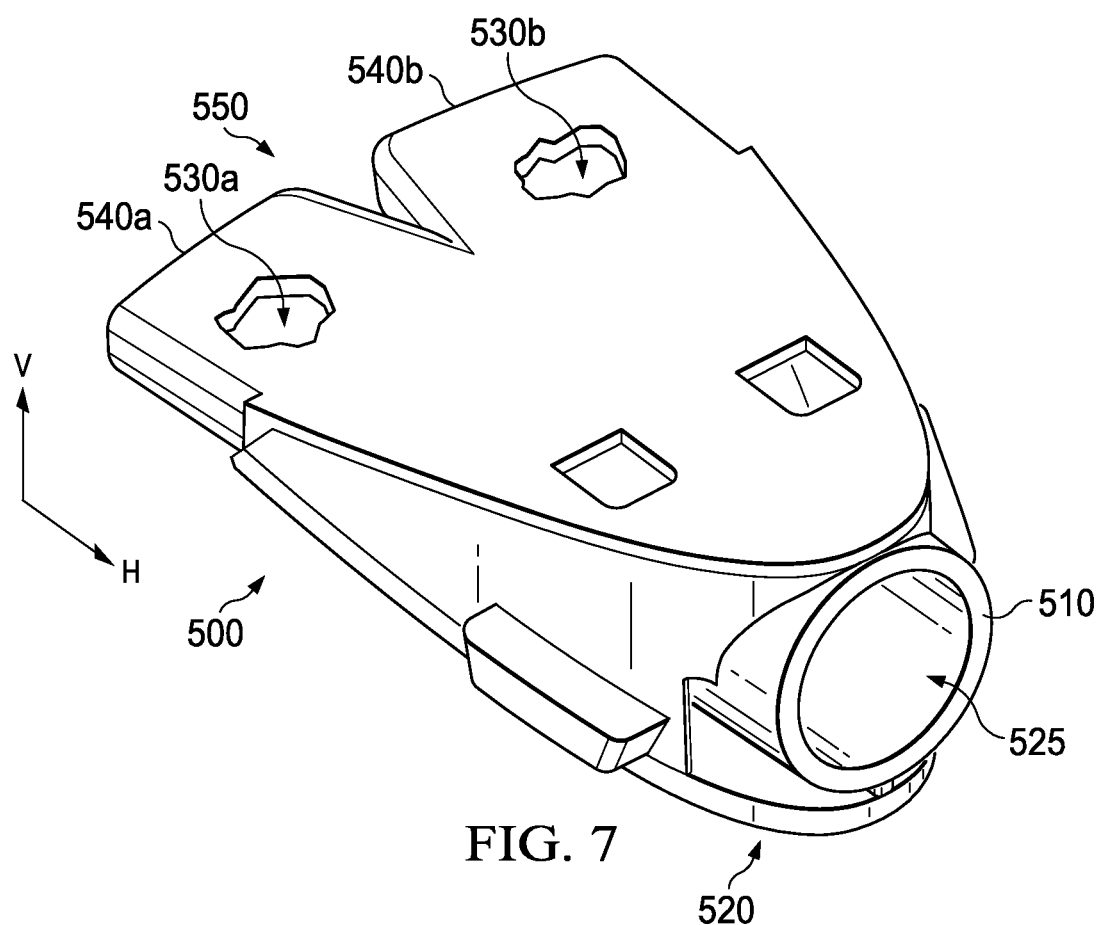
FIG. 7 is a perspective view of an alternate embodiment of the connector port shown in FIGS. 6a and 6b.

As shown in FIG. 7, the connector port 500 can have two connector port discharge end openings 540a and 540b that connect to a single connector port supply end opening 510 with a Y-shaped flowpath therebetween. The Y-shaped flowpath comprises a supply end flowpath 520 leading to two discharge end flowpaths 530a and 530b. The supply end flowpath 520 and two discharge end flowpaths 530a and 530b include converging cross-sections, such that the cross-sections of each of the flowpaths decrease in the direction of flow. As previously described, the decrease in cross-section refers to the decrease in area as the flowpath progresses from the supply end opening 510 to the discharge end opening 540 along the flowpath. The cross sections may decrease in the horizontal direction, vertical direction or both. For the connector port shown in FIG. 7, the connector port supply end flowpath 520 cross section decreases in the vertical direction V and the two connector port discharge end flowpaths 530a and 530b decrease in the horizontal H and vertical V directions.

Converging flowpaths in both the connector port and the dispensing member are preferably smoothly converging in that they converge in a continuous manner as opposed to converging in an interrupted a step like manner along the flowpath. This produces a uniform fluid flow field that exhibits a minimal pressure drop along the flowpath in the direction of flow with a maximum pressure drop occurring at the discharge end openings of the dispensing member. This helps to prevent build up where clogging is most likely to occur. The uniform flow field also exhibits a continuous increase in velocity resulting in no stagnant or recirculation areas along the flowpath which reduces clogging and prevents bacteria build up by ensuring fluid that is first in is first out. In addition, due to the uniform flow field, the force required to actuate the pump is reduced resulting in a low actuator (button) force required to dispense fluid during use as well as lessens the need for priming the pump.

Pump

Figure 8:
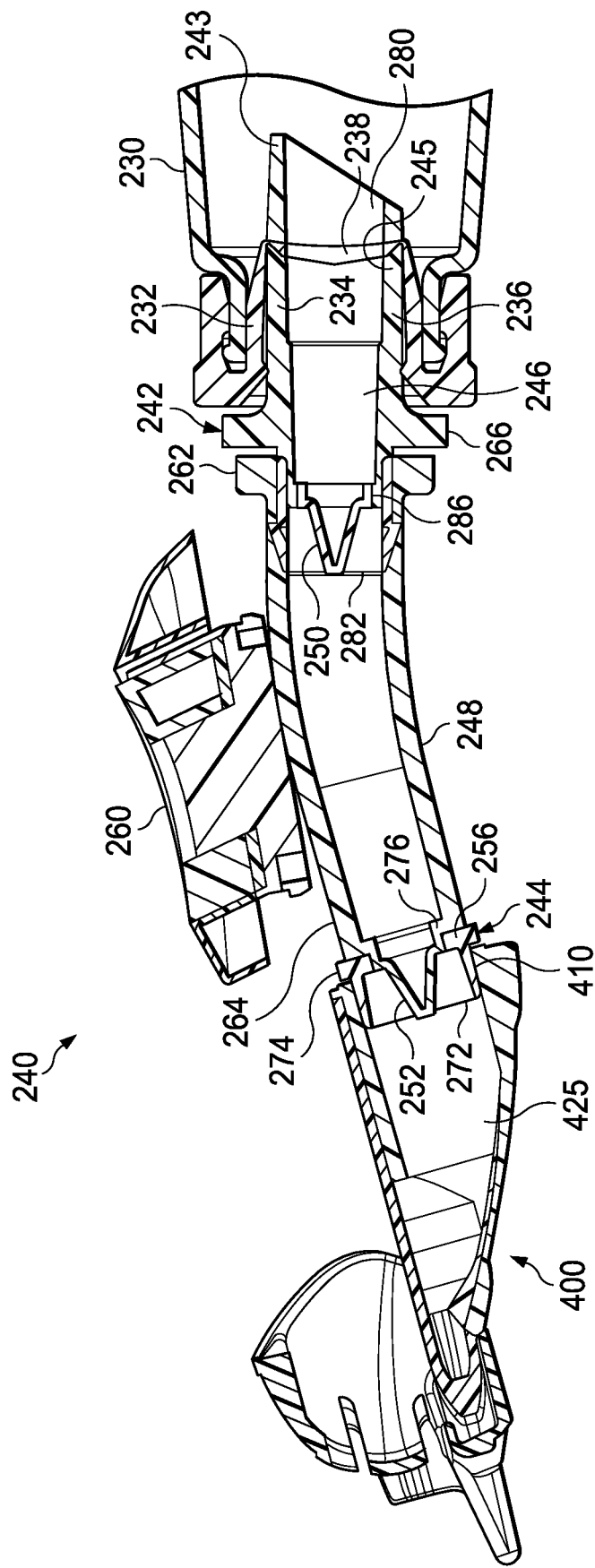
FIG. 8 is a cross-sectional view of the pump of the wet shaving razor shown in FIGS. 1-3.

The pump for the liquid dispensing razor according to the present invention is a manually actuated pump that can transport fluid by repeatedly depressing an actuator or button. An assembly view of such a pump assembly 240 is illustrated in FIG. 8. The pump assembly 240 includes a flexible tube 248 interposed between a first connector 242 and a second connector 244 and an actuator (button) 260 therebetween. A first valve 250 is disposed in the first connector 242 and a second valve 252 is disposed in the second connector 244. The first fluid connector 242 includes a tip 243 that may pierce a frangible seal 238 in the opening 232 of the fluid reservoir 230 to establish a fluid connection between the pump 240 and the fluid reservoir 230. The outer wall 245 of the first fluid connector 242 may seal against an inner wall 234 of the fluid reservoir 230 to prevent fluid from leaking into the cavity 208 of the handle 200. Accordingly, fluid is directed within an opening 246 of the first fluid connector 242, which is in fluid communication with a pump assembly 240. The elongated resilient tube 248 pumps fluid from the fluid reservoir 230 through valves 250 and 252 to the connector port 400.

An actuator 260 (e.g., a button) facilitates pumping of the fluid from the fluid reservoir 230 to the connector port 400. For example, the actuator 260 may compress the resilient elastomeric tube 248 to open the second valve 252 and release a predetermined dosage of fluid to the connector port 400. The actuator 260 may be released to return the resilient elastomeric tube 248 to its uncompressed state. As the resilient elastomeric tube 248 returns to its uncompressed state, the second valve 252 closes to prevent back flow of the fluid and corresponding contamination associated therewith and the first valve 250 opens allowing the resilient elastomeric tube 248 to fill with fluid for the next release by the actuator 260. This is a repetitive process that is fully described below.

As shown in FIG. 8, the second connector 244 is coupled to and in liquid communication with the connector port 400. For example, a first end 272 of the second connector 244 may be press fit within the connector port 400 supply end opening 410. The second connector 244 has a second end 274 with an opening 276 dimensioned to receive the second valve 252. The second end 274 of the second connector 244 is coupled to and in liquid communication with the pump 240. The elongated resilient tube 248 has a second end 264 connected to the second end 274 of the second connector 244. The second connector 244 includes a shoulder 256 to prevent the first end 272 of the second connector 244 from extending too far into the supply end opening 410 of the connector port 400. The resilient tube 248 has a first end 262 coupled to and in liquid communication with the first connector 242. The first connector 242 may be semi-rigid and have a second end 282 press fit into the first end 262 of the resilient tube 248. The first connector 242 second end 282 has an opening 286 extending through the first connector 242. The opening 286 is dimensioned to receive a first valve 250 (e.g., a duckbill valve). The first connector 242 may have a first end 280 press fit into the opening 232 of the reservoir 230. The first connector 242 first end 280 includes the tip 243 for piercing the frangible seal 238 in the reservoir opening 232. The first connector 242 includes a shoulder 266 to prevent the first end 280 of the first connector 242 from extending too far into the reservoir opening 232 and the second end 282 from extending too far into the resilient tube 248.

The valves 250 and 252 may be one way valves (e.g., check valves, clack valves, and non-return valves) that are connected in series. Examples of one way valves that may be used include, but not limited to ball check valves, swing check valves or tilting disc check valves, stop-check valves, lift-check valves, and duckbill valves. The positioning of the valves 250 and 252 within the first and second connectors 242, 244 saves space and also helps prevent the valves 250 and 252 from moving out of position.

Figure 9:
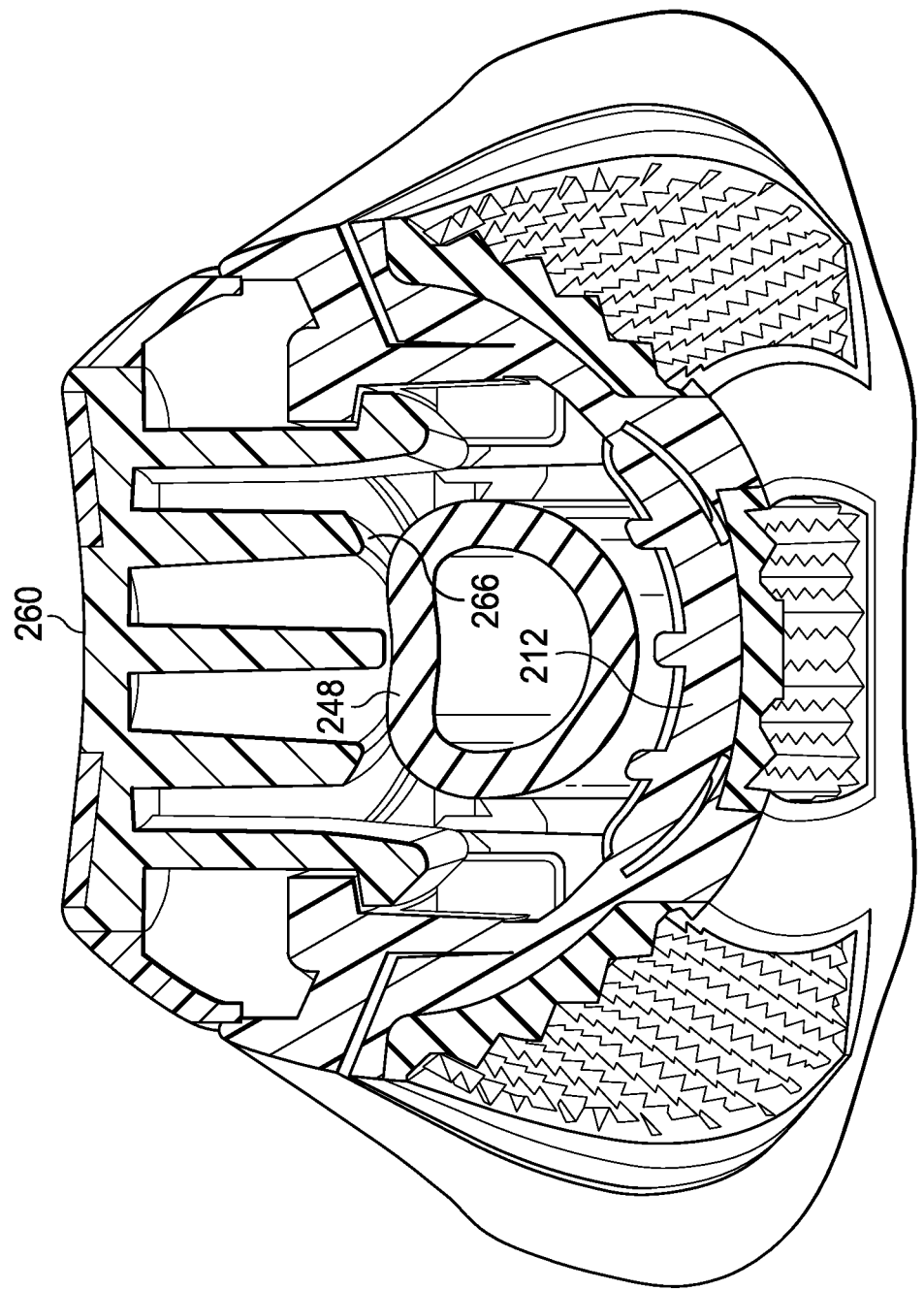
FIG. 9 is a cross-sectional view of the pump shown in FIG. 8.

In certain embodiments, the actuator 260 may directly contact and compress the resilient tube 248. FIG. 9 shows a cross section of an actuator 260 for a pump 240 according to the present invention. The bottom portion 266 of the actuator 260 may be shaped to match the inside contour of the handle cavity 208 and curved optimally front to back to minimize stress to the resilient tube 248. Although the actuator can be positioned anywhere along the length of the resilient tube 248 between the first and second valves 250, 252 it is preferably located in the center of the resilient tube 248.

When pressed, the actuator 260 compresses the resilient tube 248 opening the second valve 252, while first valve 250 remains closed. The first and second valves 250 and 252 may each have a flattened end when closed. The flattened ends open to permit liquid to pass when pressure is applied and close to prevent liquid back flow when pressure is removed (e.g., when the actuator 260 is released from the resilient tube 248). The first valve 250 opens (and the second valve 252 closes) when negative pressure is achieved within the resilient tube 248 (e.g., when the actuator 260 is released and no longer compressing the resilient tube 248, allowing it to return to its uncompressed state). The resilient properties (e.g., elongation at break and hardness) and the wall thickness may facilitate the resilient tube 248 returning to its natural state and achieve negative pressure within the resilient tube 248. When the second valve 252 is closed and the first valve 250 is open, liquid may travel from the reservoir 230, through the reservoir opening 234, through the first valve 250 and into the resilient tube 248. The positioning of a resilient tube 248 between a pair of one way valves positioned in series prevents back flow of shaving debris and microbes into the pump 240 and the reservoir 230. In certain embodiments, the resilient tube 248 may return the actuator 260 back to its original position. Accordingly, an additional return force member (e.g., a spring) is not necessarily required to return the actuator 260 back to its original position. The resilient tube 248 may be extruded or molded from materials having a Shore A hardness of about 40 to about 90 (ISO 868), including, but not limited to thermoplastic elastomers (TPEs), polyvinylchloride (PVC), silicones, rubbers, or any combination thereof. The resilient tube 248 may comprise a material having a tensile strength at break of about 8 MPa, 9 MPa, or 10 MPa to about 12 MPa, 13 MPa, or 14 MPa (ISO 37). The resilient tube 248 may comprise a material having a percent elongation at break of about 300% mm2, 400%, or 500% to about 600% mm2, 700%, or 800% (ISO 37). The resilient tube 248 may have a nominal wall thickness of about 0.5 mm, 0.75 mm, or 1 mm to about 1.25 mm, 1.5 mm, or 2 mm to provide sufficient flexibility to allow efficient compression of the resilient tube 248 by the actuator 260, but not too flexible such that the resilient tube 248 does not return to its original position after being repeatedly compressed.

Reservoir

Figure 10:
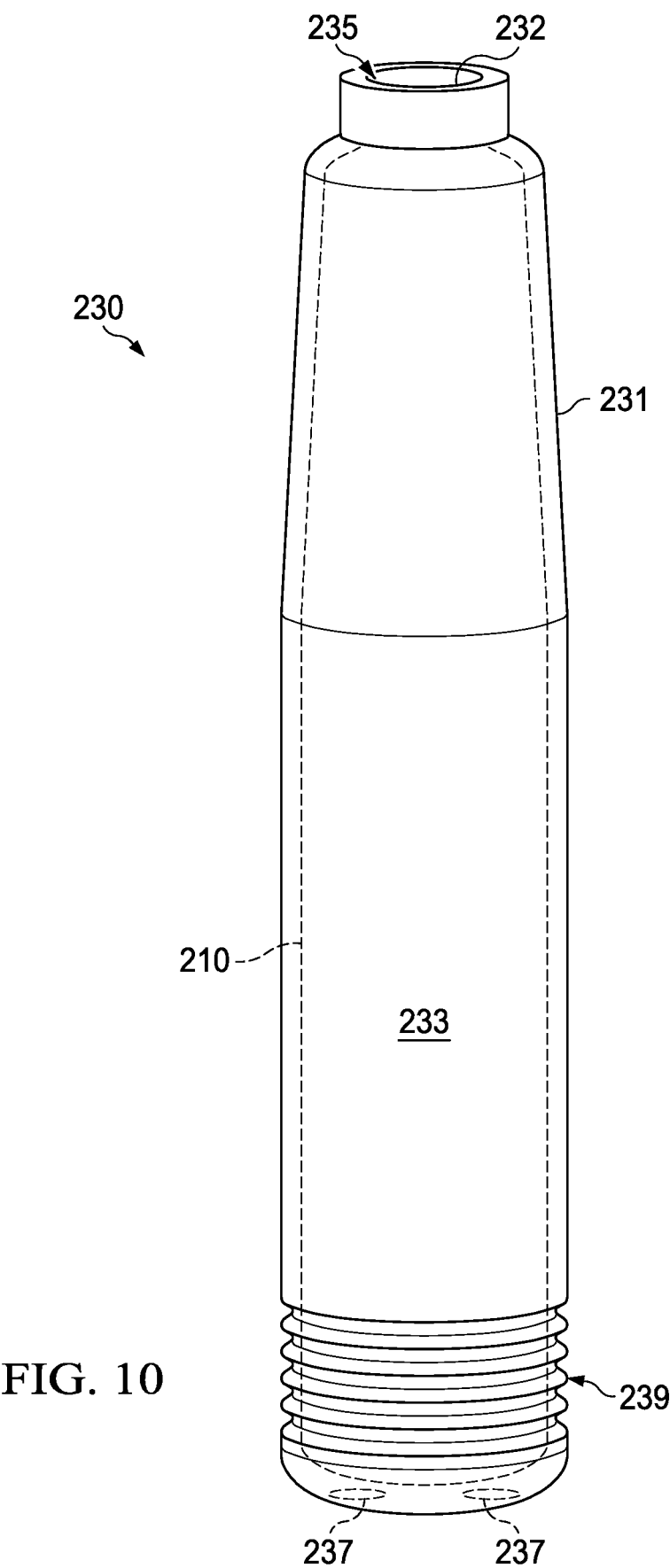
FIG. 10 is a side view of the reservoir of the wet shaving razor shown in FIGS. 1-3.

The cavity 208 includes a reservoir 230 housing a fluid 210. The reservoir 208 can include a replaceable bottle. FIG. 10 shows a reservoir 230 containing a fluid 210. The reservoir 230 includes an outer container (231), enclosing a collapsible reservoir (233). The container 231 and collapsible reservoir 233 have aligned openings which, together, form a fluid outlet (235) through which fluid may exit the collapsible reservoir (233) and container (231). One or more orifice(s) (237) in the container (231) allow air to flow into the container, thereby permitting pressure compensation as the collapsible reservoir (233) collapses. The reservoir shown in FIG. 10 also includes a plurality of ribs 239 circumscribing the bottom end of the container 231. The ribs 239 provide an outer surface that is easy to grip during removal of the container 231 from the cavity 208 and provide a collapsible accordion effect during insertion of the container 231 in the cavity 208 and connection of the fluid outlet 235 of the reservoir 230 to the first connector 242 of the pump 240. As the plurality of ribs collapse the container 231 compresses the collapsible reservoir 233 forcing fluid 210 from the collapsible reservoir 233 into the pump. This primes the pump 240, making it ready for use.

A fluid 210 (e.g., a lotion or gel) may be held within a fluid reservoir 230. Fluid reservoir 230 may be removed and replaced after the fluid 210 is consumed. The handle 200 may define a cavity 208 configured to receive the fluid reservoir 230. In certain embodiments, the fluid reservoir 230 may be a delaminating bottle or a sachet. In other embodiments, the fluid reservoir 230 may be a blow molded or injection molded plastic bottle.

As shown in FIG. 8 (previously described) the first connector 242 removably engages the fluid reservoir 230 to establish fluid connection between the fluid reservoir 230 and the pump assembly 240. The outer wall 245 of the first connector 242 may seal against an inner wall 236 of the fluid reservoir 230 to prevent fluid from leaking into the handle cavity 208. The first connector 242 includes tip 243 configured to pierce a seal (238) of the fluid reservoir 230 to establish a fluid connection between the pump assembly 240 and the fluid reservoir 230. In certain embodiments, the tip 243 may be beveled and/or angled (e.g., pyramidal, conical) to facilitate the penetration of the seal.

The container may have multiple chambers that allow fluids to mix upon being dispensed. The fluid may include shaving gels, shaving foams, shaving lotions, skin treatment compositions, conditioning aids, etc., all which may be used to prepare the skin's surface prior to the engagement of the blade with the skin. Additionally, such materials may comprise benefit agents suitable for skin and/or hair that may be useful for a number of different desirable effects including exfoliation, cooling effects, cleansing, moisturizing, warming or thermogenic effects, conditioning, and the like. Suitable benefit agents for skin and/or hair for inclusion into the fluid of the razor are disclosed in U.S. Pat. No. 6,789,321. For instance, suitable agents include but are not limited to shaving soaps, lubricants, skin conditioners, skin moisturizers, hair softeners, hair conditioners, fragrances, skin cleansers, bacterial or medical lotions, blood coagulants, anti-inflammatories, astringents, and combinations thereof. In certain embodiments, the fluid may be contained in a sachet, either disposable or reusable, that is further contained within the cavity of the handle.

Figure 11:
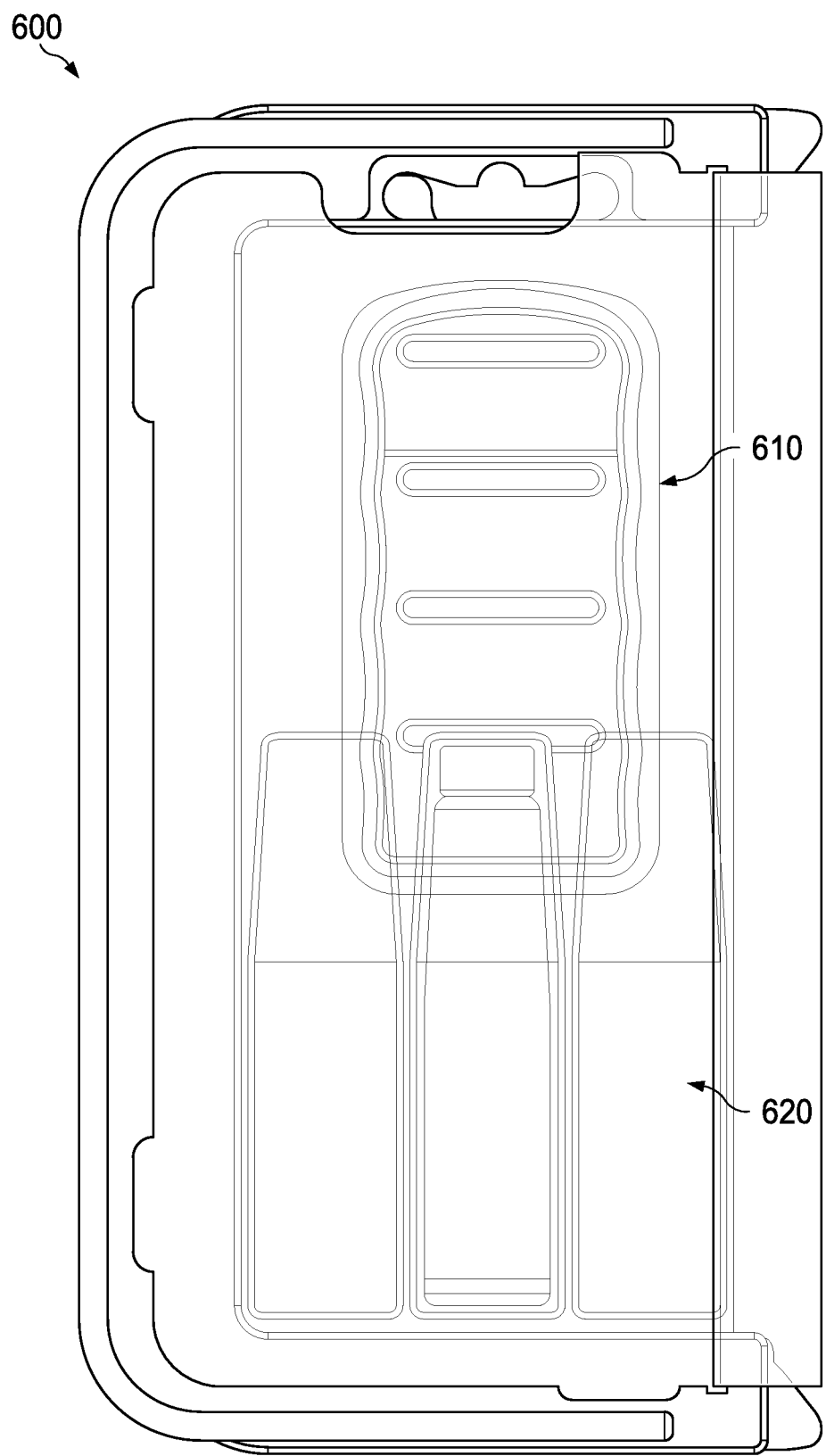
FIG. 11 is a perspective view of a package including replaceable razor cartridges and replaceable fluid reservoirs according to the present invention.

The liquid dispensing razor according to the present invention includes consumable cartridges that need to be replaced after a number of uses as a result of the blades becoming dull, the dispensing member becoming clogged or both. However, the liquid dispensing razor also includes fluid reservoirs that need to be replaced periodically. Although the disposable cartridges and replaceable fluid reservoirs can be packaged separately, they can also be packaged together and made available to consumers in a single package. For instance, replaceable cartridges 610 and replaceable fluid reservoirs 620 can be packaged together in a blister pack package 600 as illustrated in FIG. 11. The number of replaceable cartridges and replaceable fluid reservoirs per package can be the same or different. However, not to be bound by theory, the replaceable fluid reservoirs may contain a volume of fluid that correlates to the number of shaves per razor cartridge so that the consumer replaces the razor cartridge at the same time the fluid reservoir is replaced.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid dispensing razor comprising:
   a razor cartridge including a housing, the housing defining at least one aperture and including microcombs and at least one blade, the microcombs being disposed between the at least one blade and the aperture; and
   a reservoir in fluid communication with the aperture, the reservoir containing a shave care composition, the shave care composition comprising:
   water;
   from 15% to about 50%, by weight, of one or more lipophilic skin conditioning agents;
   one or more thickening agents including electrolyte sensitive polymers;
   one or more emulsifying agents; and
   one or more lubricants;
   wherein the shave care composition has a Power-Law Consistency of less than about 38 Pa·s and greater than about 23 Pa·s, such that the shave care composition is dispensable from the reservoir through the at least one aperture and capable of being distributed by the microcombs adjacent the at least one blade.

2. The liquid dispensing razor of claim 1, wherein the composition comprises from about 0.1% to about 5%, by weight, of the one or more thickening agents.

3. The liquid dispensing razor of claim 1, wherein the composition comprises from about 0.1% to about 20%, by weight, of the one or more emulsifying agents.

4. The liquid dispensing razor of claim 1, wherein the composition comprises from about 0.1% to about 8%, by weight, of the one or more lubricants.

5. The liquid dispensing razor of claim 1, further comprising salicylic acid.

6. The liquid dispensing razor of claim 5, wherein the composition comprises from about 0.001% to about 5%, by weight, of the salicylic acid.

7. The liquid dispensing razor of claim 1 wherein the electrolyte sensitive polymer is selected from the group consisting of Polyacrylamide, Hydroxyethyl Acrylate/Sodium Acryloyldimethyltaurate Copolymer, Sodium Acrylate/Sodium Acryloyldimethyl Taurate Copolymer, Ammonium Polyacrylate, Sodium Acrylate/Acryloyldimethyltaurate/Dimethylacrylamide Crosspolymer, Hydroxyethyl Acrylate/Sodium Acryloyldimethyltaurate Copolymer, Carboxylic Acid Polymers, Ammonium Acryloyldimethyltaurate/VP Copolymer, Sodium Acryloyldimethyltaurate/VP Copolymer, Ammonium Acryloyldimethyltaurate/Beheneth-25 Methacrylate Crosspolymer.

8. The liquid dispensing razor of claim 1 wherein the electrolyte sensitive polymer is Polyacrylamide.

9. The liquid dispensing razor of claim 1 wherein the lipophilic skin conditioning agent is comprised of pre-blended lipid materials.

10. The liquid dispensing razor of claim 9 where the pre-blend is composed of Petrolatum with another lipid oil chosen from mineral oil or a fatty acid ester.

11. The liquid dispensing razor according to claim 1 wherein the shave care composition has a Power-Law Index of less than about 0.5 and a Power-Law Consistency of greater than about 25 Pa·s.

12. The liquid dispensing razor according to claim 11 wherein the Power-Law Consistency is greater than about 30 Pa·s.

13. A liquid dispensing razor comprising:
a razor cartridge including a housing, the housing defining at least one aperture and including microcombs and at least one blade, the microcombs being disposed between the at least one blade and the aperture; and
a reservoir in fluid communication with the aperture, the reservoir containing a shave care composition, the shave care composition comprising:
water;
from 15% to about 50%, by weight, of one or more lipophilic skin conditioning agents;
from about 0.1% to about 5%, by weight, of one or more thickening agents;
from about 0.1% to about 20%, by weight, of one or more emulsifying agents; and
from about 0.1% to about 8%, by weight, of one or more lubricants;
wherein the shave care composition has a Power-Law Consistency of less than about 38 Pa·s and greater than about 23 Pa·s, such that the shave care composition is dispensable from the reservoir through the at least one aperture and capable of being distributed by the microcombs adjacent the at least one blade.

14. The liquid dispensing razor of claim 13, wherein the composition comprises from about 0.25% to about 3%, by weight, of the one or more thickening agents.

15. The liquid dispensing razor of claim 13, wherein the composition comprises from about 1.0% to about 12%, by weight, of the one or more emulsifying agents.

16. The liquid dispensing razor of claim 13, wherein the composition comprises from about 0.2% to about 3%, by weight, of the one or more lubricants.

17. The liquid dispensing razor according to claim 13 wherein the shave care composition has a Power-Law Index less than about 0.5 and a Power-Law Consistency of greater than about 25 Pa·s.

18. The liquid dispensing razor according to claim 17 wherein the Power-Law Consistency is greater than about 30 Pa·s.

* * * * *